United States Patent [19]
Rigg et al.

[11] Patent Number: 5,910,434
[45] Date of Patent: Jun. 8, 1999

[54] METHOD FOR OBTAINING RETROVIRAL PACKAGING CELL LINES PRODUCING HIGH TRANSDUCING EFFICIENCY RETROVIRAL SUPERNATANT

[75] Inventors: Richard J. Rigg, Mountain View; Jingyi Chen, Fremont; Jonathan S. Dando, Sunnyvale; Ivan Plavec; Sean P. Forestell, both of Menlo Park; Ernst Bohnlein, Los Altos, all of Calif.

[73] Assignee: SyStemix, Inc., Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/572,959

[22] Filed: Dec. 15, 1995

[51] Int. Cl.$^6$ .............................. C12N 5/10; C12N 15/63; C12N 15/67
[52] U.S. Cl. .................. 435/172.3; 435/7.1; 435/7.72; 435/325; 435/350; 435/357; 435/363; 435/366
[58] Field of Search .................................... 435/7.1, 7.72, 435/172.3, 325, 366, 357, 350, 363

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 4,754,065 | 6/1988 | Levenson et al. | 562/564 |
| 4,800,159 | 1/1989 | Mullis et al. | 435/91.2 |
| 5,061,620 | 10/1991 | Tsukamoto et al. | 435/7.21 |
| 5,278,056 | 1/1994 | Bank et al. | 435/172.3 |
| 5,498,537 | 3/1996 | Bresler et al. | 435/235.1 |
| 5,591,624 | 1/1997 | Barber et al. | 435/366 |
| 5,686,279 | 11/1997 | Finer et al. | 435/172.3 |
| 5,716,826 | 2/1998 | Gruber et al. | 435/320.1 |

FOREIGN PATENT DOCUMENTS

| | | |
|---|---|---|
| WO 89/07150 | 8/1989 | WIPO . |
| WO 90/02806 | 3/1990 | WIPO . |
| WO 92/05266 | 4/1992 | WIPO . |
| WO 92/08796 | 5/1992 | WIPO . |
| WO 92/14829 | 9/1992 | WIPO . |
| WO 94/19478 | 9/1994 | WIPO . |
| WO 94/28143 | 12/1994 | WIPO . |
| WO 96/04934 | 2/1996 | WIPO . |

OTHER PUBLICATIONS

Delouis, et al., "Xenotropic and amphotropic pseudotyped recombinant retrovirus to transfer genes into cells from various species" *Biochem. Biophys. Res. Commun.* (1990) 169(1):8–14.

DeMonte, et al., "Gene transfer by retrovirus–derived shuttle vectors in the generation of murine bispecific monoclonal antibodies" *Proc. Natl. Acad. Sci.* (1990) 87(8):2941–2945.

Dougherty, et al., "New Retrovirus Helper Cells with Almost No Nucleotide Sequence Homology to Retrovirus Vectors" *J. Virol.* (1989) 63(7):3209–3212.

Gelinas, et al. "Retroviral vectors for the beta–globin gene that demonstrates improved titer and expression" *Ann. N.Y. Acad. Sci.* (1990) 612:427–441.

Lehn, P.M., "Gene therapy using bone marrow transplantation: a 1990 update" *Bone Marrow Transplant* (1990) 5(5):287–293.

Muenchau, et al., "Analysis of retroviral packaging lines for generation of replication–competent virus" *Virology* (1990) 176(1):262–265.

Sorge, et al., "Amphotropic retrovirus vector system for human cell gene transfer" *Mol. Cell. Biol.* (1984) 4(9):1730–1737.

Markowitz et al., Journal of Virology 62(4):1120–1124 (1988).

Markowitz et al., Virology 167(2):400–406 (1988).

Bagnis et al., "Leukemogenicity of v–myb–transformed monoblasts cells can be modulated by normal bone marrow environment" *Oncogene* (1993) 8:737–743.

Bevec et al., "Inhibition of human immunodeficiency virus type 1 replication in human T cells by retroviral–mediated gene transfer of a dominant–negative Rev trans–activator" *Proc. Natl. Acad. Sci. USA* (1992) 89:9870–9874.

Bonnerot et al., "A β–galactosidase hybrid protein targeted to nuclei as a marker for developmental studies" *Proc. Natl. Acad. Sci. USA* (1987) 84:6795–6799.

Burns et al., "Vesicular stomatitis virus G glycoprotein pseudotyped retroviral vectors: Concentration to very high titer and efficient gene transfer into mammalian and non-mammalian cells" *Proc. Natl. Acad. Sc. USA* (1993) 90:8033–8037.

Cornetta et al., "Infection of human cells with murine amphotropic replication–competent retroviruses" *Human Gene Therapy* (1993) 4:579–588.

Cosset et al., "High–titer packaging cells producing recombinant retroviruses resistant to human serum" *J. Virol.* (1995) 69(12):7430–7436.

Cosset et al., "Retroviral retargeting by envelopes expressing an N–terminal binding domain" *J. Virol.* (1995) 69(10):6314–6322.

(List continued on next page.)

*Primary Examiner*—Johnny F. Railey, II
*Attorney, Agent, or Firm*—Morrison & Foerster LLP

[57] ABSTRACT

This invention provides a method for obtaining a recombinant retroviral packaging cell capable of producing retroviral vectors and the recombinant packaging cell obtained by the method. Also provided is a method of producing recombinant retroviral particles obtained by introducing into the packaging cells obtained according to the methods disclosed herein, a recombinant retroviral vector and propagating the resulting producer cells under conditions favorable for the production and secretion of retroviral vector supernatant. The retroviral supernatants produced by these methods also is claimed herein. This invention further provides a method for screening retroviral vector supernatant for high transduction efficiency and methods for producing retroviral vector supernatant for transducing cells with high efficiency in gene therapy applications.

23 Claims, 20 Drawing Sheets

OTHER PUBLICATIONS

Cosset et al., "Use of helper cells with two host ranges to generate high–titer retroviral vectors" *Virology* (1993) 193:385–395.

Danos et al., "Safe and efficient generation of recombinant retroviruses with amphotropic and ecotropic host ranges" *Proc. Natl. Acad. Sci. USA* (1988) 85:6460–6464.

Dranoff et al., "Vaccination with irradiated tumor cells engineered to secrete murine granulocyte–macrophage colony–stimulating factor stimulates potent, specific, and long–lasting anti–tumor immunity" *Proc. Natl. Acad. Sci. USA* (1993) 90:3539–3543.

Escaich et al., "RevM10–mediated inhibition of HIV–1 replication in chronically infected T cells" *Human Gene Therapy* (1995) 6:625–634.

Evans et al., "A neutralizable epitope common to the envelope glycoproteins of ecotropic, polytropic, xenotropic, and emphotropic murine leukemia viruses" *J. Virol.* (1990) 64(12):6176–6183.

Finer et al., "kat: A high efficiency retroviral transduction system for primary human T lymphocytes" *Blood* (1994) 83(1):43–50.

Forestell et al., "Improved detection of replication–competentretrovirus" *J. Virol. Meth.* (1996) 60:171–178.

Forestell et al., "Retroviral end–point titer is not predictive of gene transfer efficiency: implications for vector production" *Gene Therapy* (1995) 2:723–730.

Gilboa, "Retroviral gene transfer: Applications to human therapy" *Adv. Exp. Med. Biol.* (1988) 241:29–33.

"Gene Expression Technology" *Methods in Enzymology* (1991) Goeddel, et al. eds., Academic Press, Inc. New York. The title page and table of contents are enclosed herewith.

Haapala et al., "Isolation from cats of an endogenous type C virus with a novel envelope glycoprotein" *J. Virol.* (1985) 53(3):827–833.

Hoatlin et al., "Amplified and tissue–directed expression of retroviral vectors using ping–pong techniques" *J. Mol.Med.* (1995) 73:113–120.

Hodgson, "Expression Systems: A user's guide" *Bio/Techniques* (1993) 11:887–893.

Irving et al., "A reverse transcriptase–polymerase chain reaction assay for the detection and quantitation of murine retroviruses" *Bio/Technol.* (1993) 11:1042–1046.

Joshi et al., "Reduction in growth temperature minimizes instability of large plasmids containing HIV–1 proviral genomes" *BioTechniques* (1993) 14:880–886.

Kantoff et al., "Expression of human adenosine deaminase in nonhuman primates after retrovirus–mediated gene transfer" *J. Exp. Med.* (1987) 166:219–234.

Kasahara et al., "Tissue–specific targeting of retroviral vectors through ligand–receptor interactions" *Science* (1994) 266:1373–1376.

Kotani et al., "Improved methods of retroviral vector transduction and production for gene therapy" *Human Gene Therapy* (1994) 5:19–28.

Kozak, "At least six nucleotides preceding the AUG initiator codon enhance translation in mammalian cells" *J. Mol. Biol.* (1987) 196:947–950.

Lander et al., "A Mus dunni cell line that lacks sequences closely related to endogenous murine leukemia viruses and can be infected by ecotropic, amphotropic, xenotropic, and mink cell focus–forming viruses" *J. Virol.* (1984) 52(2):695–698.

Luskey et al., "Gene transfer into murine hematopoietic stem cells and bone marrow stromal cells" *Ann. N.Y. Acad. Sci.* (1990) 612:398–406.

Markowitz et al., "A safe packaging line for gene transfer: Separating viral genes on two different plasmids" *J. Virol.* (1988) 62(4):1120–1124.

Markowitz et al., "Construction and use of a safe and efficient amphotropic packaging cell line" *Virology* (1988) 167:400–406.

Marsh et al., "Retention of progenitor cell function in CD34$^+$ cells purified using a novel O–sialoglycoprotease" *Leukemia* (1992) 6(9):926–934.

Miller et al., "Improved retroviral vectors for gene transfer and expression" *BioTechniques* (1989) 7(9):980–990.

Miller et al., "Redesign of retrovirus packaging cell lines to avoid recombination leading to helper virus production" *Mol. Cell Biol.* (1986) 6(8):2895–2902.

Miller et al., "Two base changes restore infectivity to a noninfectious molecular clone of moloney murine leukemia virus (pMLV–1)" *J. Virol.* (1984) 49:214–222.

Miller, "Progress toward human gene therapy" *Blood* (1990) 76(2):271–278.

Miller, "Retrovirus packaging cells" *Human Gene Therapy* (1990) 1:5–14.

Morgenstern et al., "Advanced mammalian gene transfer: high titre retroviral vectors with multiple drug selection markers and a complementary helper–free packaging cell line" *Nucl. Acids. Res.* (1990) 18(12):3587–3596.

"Orda Reports. Recombinant DNA Advisory Committee (RAC). Data Management Report Jun. 1994" *Human Gene Therapy* (1994) 5:1293–1302.

Ott et al., "Sequence analysis of amphotropic and 10A1 murine leukemia viruses: Close relationship to mink cell focus–inducing viruses" *J. Virol.* (1990) 64(2):757–766.

Paul et al., "Increased viral titer through concentration of viral harvests from retroviral packaging lines" *Hum. Gene Therapy* (1993) 4:609–615.

*PCR: The Polymerase Chain Reaction* (1994) Mullis et al. eds., Birkhauser Press, Boston. The title page and table of contents are included herewith.

Pear et al., "Production of high–titer helper–free retroviruses by transient transfection" *Proc. Natl. Acad. Sci. USA* (1993) 90:8392–8396.

Plavec et al., "Sustained retroviral gene marking and expression in lymphoid and myeloid cells derived from transduced hematopoietic progenitor cells" *Gene Therapy* (1996) 3:717–724.

Printz et al., "Recombinant retroviral vector interferes with the detection of amphotropic replication competent retrovirus in standard culture assays" *Gene Therapy* (1995) 2:143–150.

Riele et al., "Consecutive inactivation of both alleles of the pim–1 proto–oncogene by homologous recombination in embryonic stem cells" *Nature* (1990) 348:649–651

Rigg et al., "Detection of intracellular HIV–1 Rev Protein by flow cytometry" *J. Immunol. Meth.* (1995) 188:187–195.

Rigg et al., "A novel human amphotropic packaging cell line: high tilter, complement resistance, and improved safety" *Virology* (1996) 218(1):290–295.

Sambrook et al., *Molecular Cloning.* A Laboratory Manual, 2nd ed., (1989) Cold Spring Harbor Laboratory Press, New York. A title page and table of contents are enclosed herewith.

Shinnick et al., "Nucleotide sequence of Moloney murine leukaemia virus" *Nature* (1981) 293:543–548.

Smith, "Retroviral vector–mediated gene transfer into hematopoietic cells: Prospects and issues" *J. Hematother.*(1992) 1:155–166.

Somia et al., "Generation of targeted retroviral vectors by using single–chain variable fragment: An approach to in vivo gene delivery" *Proc. Natl. Acad. Sci. USA* (1995) 92:7570–7574.

Soneoka et al., "A transient three–plasmid expression system for the production of high titer retroviral vectors" *Nucleic Acids Research* (1995) 23(4):628–633.

Sutherland et al., "Differential sensitivity of CD34 epitopes to cleavage by *Pasteurella haemolytica* glycoprotease: Implications for purification of CD34–positive progenitor cells" *Exp. Hematol.* (1992) 20:590–599.

Takeuchi et al., "Type C retrovirus inactivation by human complement is determined by both the viral genome and the producer cell" *J. Virol.* (1994) 68(12):8001–8007.

Technical Report Series No. 786 WHO, Geneva.

Vanin et al., "Characterization of replication–competent retroviruses from nonhuman primates with virus–induced T–cell lymphomas and observations regarding the mechanism of oncogenesis" *J. Virol.* (1994) 68(7):4241–4250.

Vara et al., "Expression in mammalian cells of a gene from *Streptomyces alboniger* conferring puromycin resistance" *Nucl. Acids. Res.* (1986) 14(11):4617–4624.

Xu et al., "Poor transduction efficiency of human hematopoietic progenitor cells by a high–titer amphotropic retrovirus producer cell clone" *J. Virol.* (1994) 68:7634–7636.

Yee et al., "A general method for the generation of high–titer, pantropic retroviral vectors: Highly efficient infection of primary hepatocytes" *Proc. Natl. Acad. Sci. USA* (1994) 91:9564–9568.

Forestell et al.; "Novel retroviral packaging cell lines: complementary tropisms and improved vector production for efficient gene transfer"; Gene Therapy (1997) 4, 600–610.

Chong and Vile; "Replication–competent retrovirus produced by a 'split–function' third generation amphotropic packaging cell line"; Gene Therapy (1996) 3, 624–629.

NAME
LMTNL 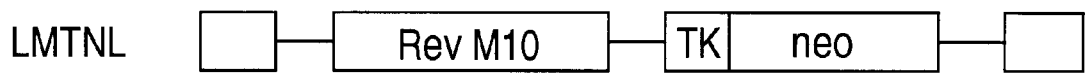
LMiLy 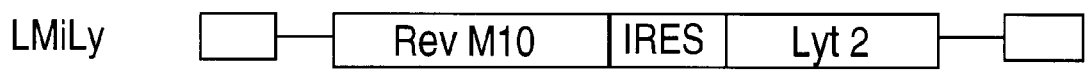
LLySN 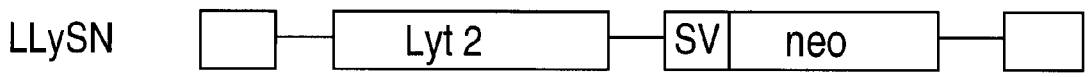
SVNLZ 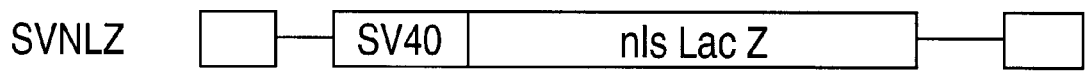
FIG. 2

| EXPT. | TEMP. (°C) | VECTOR | ULTRAFILTRATION SYSTEM | VOLUME REDUCTION | END POINT TITER (cfu/ml²) | | TRANSDUCTION EFFICIENCY (%) | |
|---|---|---|---|---|---|---|---|---|
| | | | | | BEFORE CONC. | AFTER CONC. | BEFORE CONC. | AFTER CONC. |
| 1 | 37 | SVNLZ | SARTOCON 100kD | 8.4x | $3.4 \times 10^5$ | $2.4 \times 10^6$ | ND | 4.5 |
| 2 | 37 | SVNLZ | AMICON 100kD | 6.7x | $1.6 \times 10^6$ | $7.0 \times 10^6$ | 25.9 | 14.3 |
| 3 | 37 | SVNLZ | FILTRON 300kD | 5.9x | $8.0 \times 10^6$ | $5.0 \times 10^7$ | 17.6 | 5.7 |
| 4 | 32 | SVNLZ | FILTRON 300kD | 14.3x | $3.0 \times 10^5$ | $5.7 \times 10^6$ | 22.3 | 21.1 |
| 5 | 32 | LMTNL | FILTRON 300kD | 7.5x | $2.9 \times 10^6$ | $4.4 \times 10^7$ | 28.5 | 27.0 |

FIG. 13

| TISSUE | LABEL | PACKAGING CELLS | VECTOR | COLONIES TESTED | COLONIES POSITIVE | TRANSDUCTION EFFICIENCY (%) | PCR TARGET SEQUENCE |
|---|---|---|---|---|---|---|---|
| MPB | AMPHO | PA 317 | LLySN | 24 | 4 | 17 | NEO |
| MPB | XENO | PP-X.36 | LLySN | 24 | 7 | 29 | NEO |
| MPB | AMPHO | PP-A.6 | LLySN | 24 | 11 | 46 | NEO |
| ABM | AMPHO | PP-A.6 | LMiLy | 56 | 13 | 23 | REV |
| ABM | AMPHO | PA 317 | LMiLy | 56 | 4 | 7 | REV |

MPB = MOBILIZED PERIPHERAL BLOOD
ABM = ADULT BONE MARROW FROM A CADAVER
NEO = NEOMYCIN
REV = REV M10

FIG. 14

METHOD FOR OBTAINING RETROVIRAL PACKAGING CELL LINES PRODUCING HIGH TRANSDUCING EFFICIENCY RETROVIRAL SUPERNATANT

TECHNICAL FIELD OF THE INVENTION

This invention generally relates to the derivation and use of packaging cell lines for the production of retroviral transducing supernatant.

BACKGROUND OF THE INVENTION

Human gene transfer involves the transfer of one or more therapeutic genes and the sequences controlling their expression to appropriate target cells. A number of vector systems have been developed for the transfer of the therapeutic genes for various clinical indications. In vivo gene transfer involves the direct administration of vector to the target cells within a patient. Ex vivo gene transfer entails removing target cells from an individual, modifying them ex vivo and returning the modified cells to the patient.

The majority of gene therapy protocols approved for clinical trials by the NIH Recombinant DNA Advisory Committee (RAC) have used amphotropic retroviral vectors (ORDA Reports Recombinant DNA Advisory Committee (RAC) Data Management Report, June 1994, (1994) *Human Gene Therapy* 5:1295–1302). Retroviral vectors are the vehicle of choice primarily due to the generally high rate of gene transfer obtained in experiments with cell lines and the ability to obtain stable integration of the genetic material, each ensuring that the progeny of the modified cell will contain the transferred genetic material. For a review of retroviral vectors and their use in the transfer and expression of foreign genes, see Gilboa (1988) *Adv. Exp. Med. Biol.* 241:29; Luskey et al. (1990) *Ann. N.Y. Acad. Sci.* 612:398; and Smith (1992) *J Hematother.* 1:155–166.

Many retroviral vectors currently in use are derived from the Moloney murine leukemia virus (MMLV). In most cases, the viral gag, pol and env sequences are removed from the virus, allowing for insertion of foreign DNA sequences. Genes encoded by the foreign DNA are often expressed under the control of the strong viral promoter in the LTR. Such a construct can be packaged into viral particles efficiently if the gag, pol and env functions are provided in trans by a packaging cell line. Thus, when the vector construct is introduced into the packaging cell, the gag-pol and env proteins produced by the cell assemble with the vector RNA to produce replication-defective or transducing virions that are secreted into the culture medium. The virus thus produced can infect and integrate into the DNA of the target cell, but generally will not produce infectious viral particles since it is lacking essential viral sequences.

Most of the packaging cell lines currently in use have been transfected with separate plasmids encoding gag-pol and env, so that multiple recombination events are necessary before a replication-competent retrovirus (RCR) can be produced. Commonly used retroviral vector packaging cell lines are based on the murine NIH/3T3 cell line and include PA317 (Miller & Buttimore (1986) *Mol. Cell Biol.* 6:2895; Miller & Rosman (1989) *BioTechniques* 7:980), CRIP (Danos & Mulligan (1988) *Proc. Natl Acad Sci USA* 85:6460), and gp+am12 (Markowitz et al. (1988) *Virology* 167:400). Although splitting the gag-pol and env genes within the packaging cell genome decreases the incidence of RCR, RCR is occasionally observed in clinical-scale productions of retroviral vector preparations and is a major safety concern. This is likely due, at least in part, to the fact that NIH/3T3 cells contain endogenous MMMLV sequences (Irving et al. (1993) *Bio/Technol.* 11:1042–1046) which could participate in recombination to form RCR (Cosset et al. (1993) *Virology* 193:385–395 and Vanin et al. (1994) *J. Virology* 68:4241–4250), particularly in mass culture during large-scale clinical vector production.

The range of host cells that may be infected by a retrovirus or retroviral vector is determined by the viral env protein. The recombinant virus can be used to infect virtually any cell type recognized by the env protein provided by the packaging cell, resulting in the integration of the viral genome in the transduced cell and the stable production of the foreign gene product. The efficiency of infection also is related to the level of expression of the receptor on the target cell. In general, murine ecotropic env of MMLV allows infection of rodent cells, whereas amphotropic env allows infection of rodent, avian and some primate cells, including human cells. Xenotropic vector systems utilize murine xenotropic env, and also allow infection of human cells.

The host range of retroviral vectors has been altered by substituting the env protein of the base virus with that of a second virus. The resulting, "pseudotyped" virus has the host range of the virus donating the envelope protein and expressed by the packaging cell line. For example, the G-glycoprotein from vesicular stomatitis virus (VSV-G) has been substituted for the MMLV env protein, thereby broadening the host range. See, e.g., Burns et al. (1993) *Proc. Natl. Acad. Sci USA* 90:8033–8037 and International PCT patent application Publication No. WO 92/14829.

Inconsistent results and inefficient gene transfer to some target cell types are two additional problems associated with current retroviral vector systems. For example, hematopoietic stem cells are an attractive target cell type for gene therapy because of their self-renewal capacity and their ability to differentiate into all hematopoietic lineages, thereby repopulating a patient with the modified cells. Yet retroviral gene transfer into hematopoietic stem cells has been inconsistent and disappointingly inefficient. Kantoff et al. (1987) *J. Exp. Med.* 166:219–234; Miller, A. D. (1990) *Blood* 76:271–278; and Xu et al. (1994) *J. Virol.* 68:7634. Efforts to increase gene transfer efficiency include producing higher end-point-titer retroviral vector supernatants. End-point titer is a measure of the number of active viral particles in a preparation which, when increased, should theoretically increase transduction efficiency by increasing the ratio of active virus to target cells, i.e. increasing multiplicity of infection (m.o.i.). Despite increased end-point titers, however, retroviral gene transfer efficiency (transduction efficiency) has not increased correspondingly Xu et al. (1994), supra; Paul (1993) *Hum. Gene Therapy* 4:609–615; Fraes-Lutz, et al. (1994) 22:857–865.

Efforts to increase end-point titer have included improving production of retroviral vector supernatants (see Kotani et al. (1994) *Human Gene Therapy,* 5:19–28) and physical concentration of vector particles by ultrafiltration Paul, et al. (1993), supra. and Kotani, et al. (1994) supra). It was shown that incubation of producer cells at 32° C. rather than at 37° C. yielded supernatants with higher end-point titers, but transduction efficiencies were not compared (See Kotani, et al. (1994) supra). The authors of Kotani et al. (1994) supra, postulated that the higher titers were due to a lower rate of inactivation combined with a faster rate of virion production at 32° C. In another study, transduction efficiency was measured before and after concentration of three supernatants with similar end-point titers Paul, et al. (1993) supra. In each case, concentration increased end-point titer and modestly improved the transduction efficiency. However, the transduction efficiency achieved with one of the unconcentrated supernatants was significantly higher than that achieved with the other concentrates. Paul et al. (1993) supra.

For in vivo gene therapy applications, it is important that the retroviral vector not be inactivated by human serum before infecting the target cells. Reports show that human serum inactivates a number of recombinant retroviruses, apparently via a complement pathway. Both viral envelope and producer cell components have been reported to be responsible for virus sensitivity to human complement. Takeuchi et al. (1994) *J. Virol.* 68(12):8001.

Thus, a need exists for methods of reproducibly increasing transduction efficiency and for providing stable, safe packaging cell lines for producing high transduction efficiency retroviral preparations. This invention satisfies these needs and provides related advantages as well.

SUMMARY OF THE INVENTION

This invention provides, inter alia, a method for obtaining a recombinant retroviral packaging cell capable of producing retroviral vectors. In one embodiment, the method comprises the steps of selecting a retrovirus and obtaining a cell free of endogenous retroviral nucleic acid. These steps are interchangeably performed. However, after selection of the retrovirus, a minimal gag-pol open reading frame (ORF) insert is isolated from the retrovirus. Alternatively, a nucleic acid molecule coding for functionally equivalent retroviral minimal ORF can be isolated and used in the methods disclosed herein. In the same manner, a minimal env ORF is isolated from wild type retroviral or an equivalent nucleic acid molecule is obtained. The minimal ORF nucleic acid molecules are then amplified, either by insertion into a suitable replication vector or plasmid and replication of a host cell containing the vector and/or plasmid or by other non-biological methods (PCR). After amplification, and consistent with the method of amplification, the minimal ORF nucleic acid molecules are inserted into a cell preselected to be devoid of endogenous retroviral nucleic acid. The transformed cells are then propagated under conditions favorable for expression of the minimal retroviral gag-pol and env ORF.

Suitable candidate packaging cell lines include, but are not limited to mammalian cells such as COS, Vero, HT-1080, D17 MRC-5, FS-4, TEG71, human embryonic kidney (293), and HeLa.

In further embodiment of this method, the cells that produce high levels of the retroviral gag-pol protein and the retroviral env protein are identified or selected for by assaying for gag-pol and/or env ORF translation products in the supernatant. This invention also provides the recombinant packaging cell obtained by the methods in all various embodiments described herein, including the amphotropic cell line designate ProPak-A and the xenotropic packaging cell line designated ProPak-X. Other embodiments of the packaging cell lines produced by the methods disclosed herein are packaging cell lines characterized by having the ability to produce transducing supernatant that is: resistance to human complement; having a transducing efficiency of greater than or equal to 50% when assayed on NIH/3T3 cells; or greater than that achieved on PA317-based cells, or having a transducing efficiency of greater than or equal to 20% when assayed on 293 cells; and being substantially free of RCR after interaction of retroviral vector sequences and continuous culture of more than 2 weeks with an indicator cell line.

Further provided by this invention is a method of producing recombinant retroviral particles obtained by introducing into the packaging cells obtained according to the methods disclosed herein, a recombinant retroviral vector and propagating the resulting producer cells under conditions favorable for the production and secretion of retroviral vector supernatant. The retroviral supernatants produced by these methods also is claimed herein.

This invention also provides a method for screening retroviral vector supernatant for high transduction efficiency and methods for producing retroviral vector supernatant for transducing cells with high efficiency in gene therapy applications.

DESCRIPTION OF THE FIGURES

FIG. 2 shows the structure of the several of retroviral vectors used in this study. Open boxes represent the Moloney viral elements, LTR sequences; RevM10, transdominant mutant of the HIV Rev protein; TK, Herpes Simplex virus-1 thymidine kinase promoter; neo, neomycin phosphotransferase; SV40, simian virus 40 early promoter; nls Lac Z, LacZ with a nuclear localization signal;IRES: internal ribosomal entry site.

FIG. 3A is a comparison of end-point titer and transduction efficiency for SVNLZ supernatants measured on NIH/3T3 cells. FIG. 3B is a comparison of transduction efficiencies measured on NIH/3T3, HeLa or Jurkat cells for three LMTNL supernatants with the end-point titer measured on NIH/3T3 cells. IE+05 means a dilution of $1\times10^{-5}$, IE+06 means a dilution of $1\times10^{-6}$, etc. Error bars show the standard error for three samples.

FIG. 13 is a table comparing end-point titer and transduction efficiency for concentrated retroviral supernatant produced from PA317 packaging cell line transduced with various retroviral vectors and cultured at either 32 or 37° C. and concentrated using various concentration systems.

FIG. 14 shows the results of the methyl cellulose assay performed on CD34+ blood cells transduced with retroviral supernatant of this invention.

FIG. 18A shows spinoculation with single supernatants. FIG. 18B shows spinoculation with single or mixed (ampho+xeno) supernatant.

MODES(S) FOR CARRYING OUT THE INVENTION

Definitions

Figure 1:
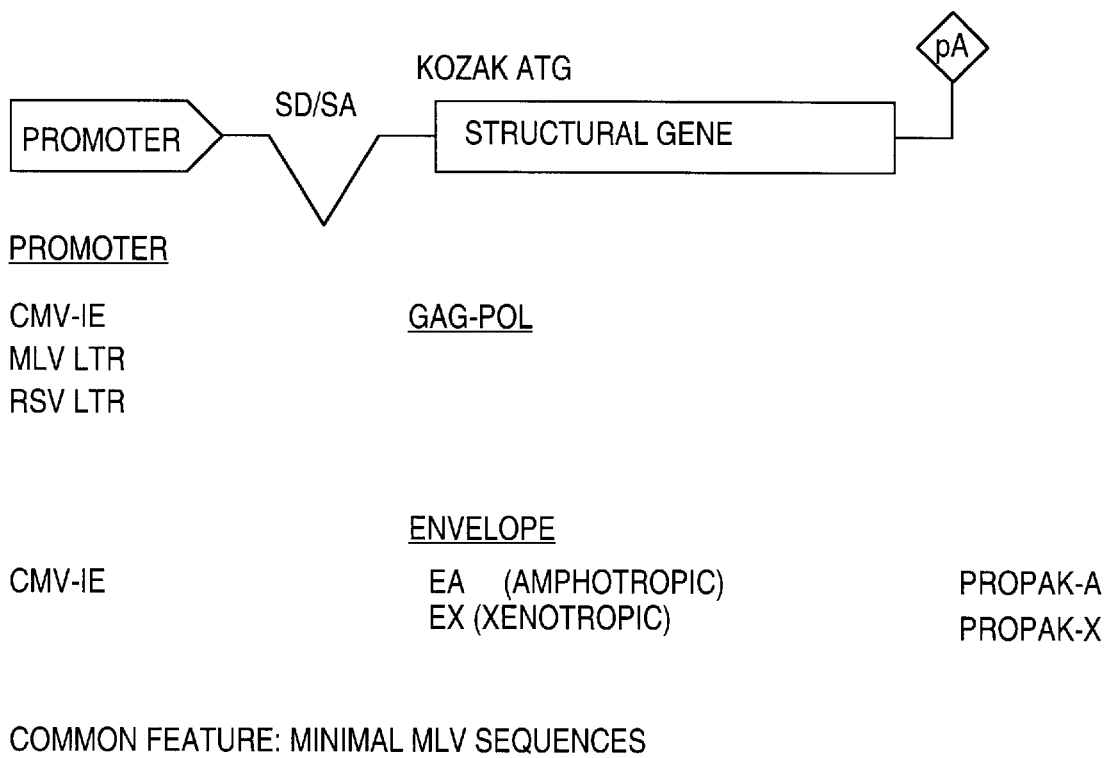
FIG. 1 schematically shows the plasmid constructs that were used for as insertion plasmids for construction of the packaging cell lines ProPak-A and Pro-Pak-X. CMV-IE denotes cytomegalovirus immediate early promoter. SD/SA denotes splice donor/splice acceptor site. MLV is the murine leukemia viral promoter present in the viral LTR. RSV LTR is the LTR promoter of Rous Sarcoma Virus. SV40 denotes the simian virus 40 early promoter. pA is the polyadenylation tail.

Unless otherwise specified herein, common definitions are intended by the words and terms used herein. For example, "retrovirus" denotes a class of viruses which use RNA-directed DNA polymerase, or "reverse transcriptase" to copy a viral RNA genome into a double-stranded DNA intermediate which can be incorporated into chromosomal DNA (a "provirus") of an avian or mammalian host cell. Retrovirus also exist as free virions, that contain the structural and enzymatic proteins of the retrovirus (including reverse transcriptase), two copies of the viral genome, and portions of the host cell's plasma membrane in which is embedded the viral envelope glycoprotein. Many such retroviruses are known to those skilled in the art and are described, for example, in Weiss et al., eds, *RNA Tumor Viruses,* 2nd ed., Cold Spring Harbor Press, Cold Spring Harbor, N.Y. (1984 and 1985). Plasmids containing retroviral genomes also are widely available, from the American Type Culture Collection (ATCC) and other sources as described in Gacesa and Ramji, *Vectors: Essential Data,* John Wiley & Sons, New York (1994). The nucleic acid sequences of a large number of these viruses are known and are generally available from databases such as GENBANK, for example. The complete nucleic acid sequence of the MMLV is known in the art.

"Packaging cell line" is a recombinant cell line containing expressing retroviral gag, pot and env nucleic acid. Because the packaging cell line lacks the retroviral nucleic acid coding for packaging signal, infectious virions cannot be produced.

A "producer cell" is a packaging cell as defined above containing retroviral gag, pol, and env nucleic acid incorporated into the cellular genome and a replication-defective retroviral vector. The producer cell produces infectious retroviral-based particles containing "foreign", such as therapeutic or marker genes (i.e., non-retroviral) nucleic acid.

A "target cell" is a cell to be transduced with a recombinant retroviral vector. Thus, target cells may be, for example, a cell line used for assessing the quality of a retroviral vector preparation, a primary cell for genetic modification ex vivo, or a cell within a patient that will be modified by in vivo introduction of a retroviral vector.

The terms "polynucleotide", "oligonucleotide", "nucleic acids" and "nucleic acid molecules" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term polynucleotide, as used herein, refers interchangeably to double- and single-stranded molecules.

Unless otherwise specified or required, any embodiment of the invention described herein that is a polynucleotide encompasses both the double-stranded form and each of two complementary single-stranded forms known or predicted to make up the double-stranded form.

A "gene" can refer to a polynucleotide or a portion of a polynucleotide comprising a sequence that encodes a protein. It is often desirable for the gene also to comprise a promoter operatively linked to the coding sequence in order to effectively promote transcription. Enhancers, repressors and other regulatory sequences also can be included in order to modulate activity of the gene, as is well known in the art (see, e.g., the references cited herein).

A "detectable marker" gene is a gene that allows cells carrying the gene to be specifically detected (i.e., to be distinguished from cells which do not carry the marker gene). A large variety of such marker genes are known in the art. Preferred examples of such marker genes encode proteins appearing on cellular surfaces, thereby facilitating simplified and rapid detection and/or cellular sorting.

A "selectable marker" gene is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative sliceable markers are known in the art, some of which are described herein.

In the context of polynucleotides, a "linear sequence" or a "sequence" is an order of nucleotides in a polynucleotide in a 5' to 3' direction in which residues that neighbor each other in the sequence are contiguous in the primary structure of the polynucleotide. A "partial sequence" is a linear sequence of part of a polynucleotide which is known to comprise additional residues in one or both directions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogsteen binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

Hybridization reactions can be performed under conditions of different "stringency". Conditions that increase the stringency of a hybridization reaction are widely known and published in the art: See, for example, Sambrook et al. (1989) infra Examples of relevant conditions include (in order of increasing stringency): incubation temperatures of 25° C., 32° C., and 37° C.

"$T_m$" is the temperature in degrees Centigrade at which 50% of a polynucleotide duplex made of complementary strands hydrogen bonded in an antiparallel direction by Watson-Crick base paring dissociates into single strands under the conditions of the experiment. $T_m$ may be predicted according to standard formula; for example:

$$T_m = 81.5 + 16.6\log[Na^+] + 0.41(\% \text{ G/C}) - 0.61(\% \text{ F}) - 600/L$$

where $Na^+$ is the cation concentration (usually sodium ion) in mol/L; (% G/C) is the number of G and C residues as a percentage of total residues in the duplex; (% F) is the percent formamide in solution (wt/vol); and L is the number of nucleotides in each strand of the duplex.

A linear sequence of nucleotides is "identical" to another linear sequence, if the order of nucleotides in each sequence is the same, and occurs without substitution, deletion, or material substitution. It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution. An RNA and a DNA polynucleotide have identical sequences when the sequence for the RNA reflects the order of nitrogenous bases in the polyribonucleotide, the sequence for the DNA reflects the order of nitrogenous bases in the polydeoxyribonucleotide, and the two sequences satisfy the other requirements of this definition. Where at least one of the sequences is a degenerate oligonucleotide comprising an ambiguous residue, the two sequences are identical if at least one of the alternative forms of the degenerate oligonucleotide is identical to the sequence with which it is being compared. For example, AYAAA is identical to ATAAA, if AYAAA is a mixture of ATAAA and ACAAA.

When comparison is made between polynucleotides, it is implicitly understood that complementary strands are easily generated, and the sense or antisense strand is selected or predicted that maximizes the degree of identity between the polynucleotides being compared. For example, where one or both of the polynucleotides being compared is double-stranded, the sequences are identical if one strand of the first polynucleotide is identical with one strand of the second polynucleotide. Similarly, when a polynucleotide probe is described as identical to its target, it is understood that it is the complementary strand of the target that participates in the hybridization reaction between the probe and the target.

A linear sequence of nucleotides is "essentially identical" to another linear sequence, if both sequences are capable of hybridizing to form duplexes with the same complementary polynucleotide. Sequences that hybridize under conditions of greater stringency are more preferred. It is understood that hybridization reactions can accommodate insertions, deletions, and substitutions in the nucleotide sequence. Thus, linear sequences of nucleotides can be essentially identical even if some of the nucleotide residues do not precisely correspond or align. Sequences that correspond or align more closely to the invention disclosed herein are comparably more preferred. Generally, a polynucleotide region of about 25 residues is essentially identical to another region, if the sequences are at least about 80% identical; more preferably, they are at least about 90% identical; more preferably, they are at least about 95% identical; still more preferably, the sequences are 100% identical. A polynucleotide region of 40 residues or more will be essentially identical to another region, after alignment of homologous portions if the sequences are at least about 75% identical; more preferably, they are at least about 80% identical; more preferably, they are at least about 85% identical; even more preferably, they are at least about 90% identical; still more preferably, the sequences are 100% identical.

In determining whether polynucleotide sequences are essentially identical, a sequence that preserves the functionality of the polynucleotide with which it is being compared is particularly preferred. Functionality can be determined by different parameters. For example, if the polynucleotide is to be used in reactions that involve hybridizing with another polynucleotide, then preferred sequences are those which hybridize to the same target under similar conditions. In general, the $T_m$ of a DNA duplex decreases by about 10° C.

for every 1% decrease in sequence identity for duplexes of 200 or more residues; or by about 50° C. for duplexes of less than 40 residues, depending on the position of the mismatched residues. Essentially identical sequences of about 100 residues will generally form a stable duplex with each other's respective complementary sequence at about 200° C. less than $T_m$; preferably, they will form a stable duplex at about 15° C. less; more preferably, they will form a stable duplex at about 100° C. less; even more preferably, they will form a stable-duplex at about 50° C. less; still more preferably, they will form a stable duplex at about $T_m$. In another example, if the polypeptide encoded by the polynucleotide is an important part of its functionality, then preferred sequences are those which encode identical or essentially identical polypeptides. Thus, nucleotide differences which cause a conservative amino acid substitution are preferred over those which cause a non-conservative substitution, nucleotide differences which do not alter the amino acid sequence are more preferred, while identical nucleotides are even more preferred. Insertions or deletions in the polynucleotide that result in insertions or deletions in the polypeptide are preferred over those that result in the down-stream coding region being rendered out of phase; polynucleotide sequences comprising no insertions or deletions are even more preferred. The relative importance of hybridization properties and the encoded polypeptide sequence of a polynucleotide depends on the application of the invention.

A polynucleotide has the same "characteristics" of another polynucleotide if both are capable of forming a stable duplex with a particular third polynucleotide under similar conditions of maximal stringency. Preferably, in addition to similar hybridization properties, the polynucleotides also encode essentially identical polypeptides.

"Conserved" residues of a polynucleotide sequence are those residues which occur unaltered in the same position of two or more related sequences being compared. Residues that are relatively conserved are those that are conserved amongst more related sequences than residues appearing elsewhere in the sequences.

"Related" polynucleotides are polynucleotides that share a significant proportion of identical residues.

A "probe" when used in the context of polynucleotide manipulation refers to an oligonucleotide which is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is an oligonucleotide, generally with a free 3' —OH group, that binds to a target potentially present in a sample of interest by hybridizing with the target, and thereafter promotes polymerization of a polynucleotide complementary to the target.

Processes of producing replicate copies of the same polynucleotide, such as PCR or gene cloning, are collectively referred to herein as "amplification" or "replication". For example, single or double-stranded DNA may be replicated to form another DNA with the same sequence. RNA may be replicated, for example, by an RNA-directed RNA polymerase, or by reverse-transcribing the DNA and then performing a PCR. In the latter case, the amplified copy of the RNA is a DNA with the identical sequence.

A "polymerase chain reaction" ("PCR") is a reaction in which replicate copies are made of a target polynucleotide using one or more primers, and a catalyst of polymerization, such as a reverse transcriptase or a DNA polymerase, and particularly a thermally stable polymerase enzyme. Generally, a PCR involves reiteratively forming three steps: "annealing", in which the temperature is adjusted such that oligonucleotide primers are permitted to form a duplex with the polynucleotide to be amplified; "elongating", in which the temperature is adjusted such that oligonucleotides that have formed a duplex are elongated with a DNA polymerase, using the polynucleotide to which they've formed the duplex as a template; and "melting", in which the temperature is adjusted such that the polynucleotide and elongated oligonucleotides dissociate. The cycle is then repeated until the desired amount of amplified polynucleotide is obtained. Methods for PCR are taught in U.S. Pat. Nos. 4,683,195 (Mullis) and 4,683,202 (Mullis et al.).

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements are known in the art. For example, a "promoter" is an example of a control element. A promoter is a DNA region capable under certain conditions of binding RNA polymerase and initiating transcription of a coding region located downstream (in the 3' direction) from the promoter. Retroviral long terminal repeat sequences (LTR) contain strong promoters that are suitably used in the inventions described herein.

"Operatively linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

The "gag" gene of a retrovirus refers to the 5' gene on retrovirus genomes and is an abbreviation for group-specific antigens. It is translated to give a precursor polyprotein which is subsequently cleaved to yield three to five capsid proteins.

The "pol" gene refers to a gene encoding a polymerase. Thus, the pol gene encodes for a retrovirus reverse transcriptase and also encodes the IN protein needed for viral integration into cell DNA.

The "env" or envelope region of a retrovirus genome codes for the envelope proteins. For the purpose of this invention, the "env" gene is to include not only the naturally occurring env sequence from a virus, but also modifications to the env gene, such as env genes that are modified to alter target specificity of retrovirus or alternative env genes that are used to generate "pseudotyped" retrovirus. Preferred retroviral env genes for use in this invention include, but are not limited to amphotropic env, murine xenotropic, env, Gibbon Ape Leukemia virus (GALV) env and the VSV-G protein.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

The "biochemical function" or "biological activity" of a polypeptide includes any feature of the polypeptide detectable by suitable experimental investigation. "Altered" biochemical function can refer to a change in the primary, secondary, tertiary, or quaternary structure of the polypeptide; detectable, for example, by molecular weight determination, circular dichroism, antibody binding, difference spectroscopy, or nuclear magnetic resonance. It can also refer to a change in reactivity, such as the ability to catalyze a certain reaction, or the ability to bind a cofactor, substrate, inhibitor, drug, hapten, or other polypeptide. A substance may be said to "interfere" with the biochemical function of a polypeptide if it alters the biochemical function of the polypeptide in any of these ways.

A "fusion polypeptide" is a polypeptide comprising regions in a different position in the sequence than occurs in nature. The regions may normally exist in separate proteins and are brought together in the fusion polypeptide; or they may normally exist in the same protein but are placed in a new arrangement in the fusion polypeptide. A fusion polypeptide may be created, for example, by chemical synthesis, or by creating and translating a polynucleotide in which the peptide regions are encoded in the desired relationship.

An "isolated" polynucleotide, polypeptide, protein, antibody, nucleic acid, or other substance refers to a preparation of the substance devoid of at least some of the other components that may also be present where the substance or a similar substance naturally occurs or is a purification technique to enrich it from a source mixture. Enrichment can be measured on an absolute basis, such as weight per volume of solution, or it can be measured in relation to a second, potentially interfering substance present in the source mixture; A substance can also be provided in an isolated state by a process of artificial assembly, such as by chemical synthesis or recombinant expression.

A polynucleotide used in a reaction, such as a probe used in a hybridization reaction, a primer used in a PCR, or a polynucleotide present in a pharmaceutical preparation, is referred to as "specific" or "selective" if it hybridizes or reacts with the intended target more frequently, more rapidly, or with greater duration than it does with alternative substances. Similarly, a polypeptide is referred to as "specific" or "selective" if it binds an intended target, such as a ligand, hapten, substrate, antibody, or other polypeptide more frequently, more rapidly, or with greater duration than it does to alternative substances. An antibody is referred to as "specific" or "selective" if it binds via at least one antigen recognition site to the intended target more frequently, more rapidly, or with greater duration than it does to alternative substances. A polynucleotide, polypeptide, or antibody is said to "selectively inhibit" or "selectively interfere with" a reaction if it inhibits or interferes with the reaction between particular substrates to a greater degree or for a greater duration than it does with the reaction between alternative substrates.

A "cell line" or "cell culture" denotes higher eukaryotic cells grown or maintained in vitro. It is understood that the descendants of a cell may not be completely identical (either morphologically, genotypically, or phenotypically) to the parent cell.

The term "primate" as used herein refers to any member of the highest order of mammalian species. This includes (but is not limited to) prosimians, such as lemurs and lorises; tarsioids, such as tarsiers; new-world monkeys, such as squirrel monkeys (Saimiri sciureus) and tamarins; old-world monkeys such as macaques (including Macaca nemestrina, Macaca fascicularis, and Macaca fuscata); hylobatids, such as gibbons and siamangs; pongids, such as orangutans, gorillas, and chimpanzees; and hominids, including humans.

"Mean residence time" is the average amount of time the media spends in contact with the cells. The optimal mean residence time is determined by the following competing considerations: 1) the length of time required to accumulate sufficient transducing virus to yield the highest transducing efficiency of the target cells and 2) the nutritional demands of the cells. For example, the optimal mean residence time for PA317 cells is from about 2.5 to about 3.5 hours and from about 7.5 to about 8.5 for ProPak cells, each at a cell density of about $1\times10^6$ cell/ml. Optimal is about 3.0 and 8.0 hours, respectively. The optimal mean residence time will decrease as cell densities increase.

DETAILED DESCRIPTION OF THE INVENTION

This invention provides a method for obtaining a safe recombinant retroviral packaging cell capable of producing retroviral-based vectors and retroviral vector supernatant. The method comprises the steps of selecting a retrovirus that will provide the retroviral env and gag-pol oligonucleotide sequences for the recombinant production of retroviral env and gag-pol gene products and obtaining a cell free of endogenous related retroviral nucleic acids or oligonucleotides of the same retroviral type. Although any retrovirus can be suitably used in the method of this invention presently described is the use of murine moloney leukemia virus (MMLV). Thus, if any of gag, pol or env genes are to be derived from a MMLV, the candidate packaging cell should be screened for absence of endogenous MMLV retroviral nucleic acid and those sequences closely related to MMLV such that recombination would produce replication competent retrovirus.

The env determines the target cell specificity of the recombinant retrovirus particle and will, therefore, be selected to provide optimal transduction of the target cells of interest. env may be the MMLV amphotropic env for any env capable of combining to form infectious "pseudotyped" retrovirus particles. For example, MMLV amphotropic and murine xenotropic retroviral vectors are known to infect human cells. Other env genes of interest include Gibbon Ape Leukemia Virus (GALV), RD114, FeLV-C, FeLV-B, BLV, HIV-1, VSV-G. See PCT Publication No. WO 92/14829 (page 25, line 1 through 1 through page 34, line 1). In addition, the env gene may be modified to more specifically target the recombinant retrovirus to the target cell of interest. For, example, the env protein may be modified by combination with an antibody binding site specific for a cell surface antigen on the target cells of interest, e.g. an anti-CD34 antibody for targeting to hematopoietic stem and progenitor cells. Cossett et al. (1995) *J. Virol.* 69:6314–6322 and Kasahara, et al. (1994) *Science* 266:1373–1376.

For clinical gene therapy applications it is important that the retroviral vector sequences and structural gene sequences be incapable of recombining to form replication competent retrovirus (RCR). By introducing the gag-pol and env gene sequences into the packaging cell separately, so they integrate in different areas of the packaging cell genome, the rate of RCR formation is decreased since multiple recombination events are required to generate RCR. Nevertheless, RCR are sometimes found in recombinant retroviral vector preparations. One possible reason is the presence of endogenous retroviral sequences in the murine cells (NIH/3T3) that are the basis for most commonly used packaging cell lines, which may recombine with the introduced retroviral sequences. Cossett et al. (1995) *J. Virol.* 69(12):7430. Therefore, the safe packaging cells of the present invention are generated from a cell line lacking endogenous retroviral sequences which would be capable of producing RCR by recombination with introduced retroviral sequences.

Thus, in one embodiment, the packaging cells of the present invention are derived from a cell line having no detectable endogenous retroviral sequences related to MMLV. In addition, the cell line preferably is screened for the ability to stably express high levels of gag-pol and env proteins, as described in the Examples herein. Preferably the cell line will be a non-murine cell line, more preferably a primate cell line, and most preferably a human cell line. The inventors have found that human 293 cells are free of retroviral sequences related to MMLV, and when used as the basis for stable packaging cells, are able to produce high transduction efficiency retroviral vectors.

A cell free of related retroviral nucleic acid is obtained by screening a candidate cell for endogenous retroviral nucleic acid using methods well known to those in skill in the art and exemplified below. For example, several available cell lines such as the *Mus dunni* tail fibroblasts (see Lander and Chattopahyah (1984) *J. Virol.* 52:695–698) are reportedly free of endogenous retroviral nucleic acid and thus, are suitably used in the methods disclosed herein. Alternatively, one of skill in the art can determine if the cell line contains endogenous retroviral nucleic acid by isolating a nucleic acid sample from the candidate cell line and probing for the endogenous DNA or RNA using methods such as traditional Southern and Northern hybridization analysis or the polymerase chain reaction ("PCR"), using retroviral specific probes and when available, commercially available PCR kits (Invitrogen, San Diego, Calif.). Southern and Northern hybridization analysis is described, for example in Sambrook et al. (1989) infra. PCR methods are described in *Gene Expression Technology*, Goeddel, et al. eds., Academic Press, Inc. New York (1991). A cell is free of endogenous related retroviral nucleic acid if no hybridization is detected, even at low stringency conditions of 500 mM sodium ions,or if the primer used for the PCR analysis does not provide amplified nucleic acid. Preferably highly conserved sequences spanning viral LTR, packaging sequence and gag-pol gene regions are used as probes.

The candidate cell is of any suitable type, i.e., murine, non-murine, mammalian, primate, canine and human, provided that the cell line lack endogenous retroviral sequences, grows well in culture, can be transfected or transduced with the appropriate gag-pol and env expression constructs and can express the viral proteins. The candidate cell line is preferably primate, and most preferably human. It has been found that primate and preferably human-based packaging cells can be used to produce retroviral vectors resistant to human complement.

In addition, the method further comprises using minimal gag-pol and env and sequences to further decrease the chances of recombination to produce RCR. A minimal gag-pol open reading frame (ORF) and minimal env ORF are obtained from the selected retrovirus. The minimal ORF of the retroviral sequences are defined to include only those retroviral sequences from the ATG through the stop codon of the gene with no flanking sequences. Fragments of the gene as well as biological equivalents thereof also can be used provided that functional protein is produced when introduced into the candidate packaging cell line. In one embodiment, isolated retroviral nucleic acid coding for the minimal gag-pol and env ORF is selected for use. In a preferred embodiment, the nucleic acid is selected from MMLV and the minimal sequences are determined to consist of nucleotides from about 621 to 5837 (gag-pol) and about nucleotides 37 to 2000 (env). It should be understood, although not always explicitly stated, that nucleic acid sequences or molecules that are "equivalent" are determined to produce the same phenotypic effect as the isolated minimal ORF described herein, can be utilized as the minimal ORF sequences in the methods described herein. For example, altered, but phenotypically equivalent nucleic acid molecules are referred to "equivalent nucleic acids".

The minimal gag-pol and env ORF nucleic acid molecules can be isolated using the technique described in the experimental section described below or replicated using PCR (Perkin-Elmer) and published sequence information. For example, the sequence can be chemically replicated using PCR (Perkin-Elmer) which, in combination with the synthesis of oligonucleotides, allows easy reproduction of DNA sequences. The PCR technology is the subject matter of U.S. Pat. Nos. 4,683,195, 4,800,159, 4,754,065, and 4,683,202 and described in *PCR: The Polymerase Chain Reaction* Mullis et al. eds., Birkhauser Press, Boston (1994) and references cited therein. As is apparent to those of skill in the art, modifications and/or additions to the viral sequences are made to facilitate expression and isolation of the amplified DNA.

It is conceived that amphotropic and xenotropic cell lines are produced by this method and is determined by the selection of the env gene. Thus, the selection of the gag-pol and env gene are not restricted to isolation from the same virus, or the same virus type. An example of an amphotropic-producing packaging cell line produced by this method is ProPak-A and an example of a xenotropic packaging cell line, also produced by this method, is ProPak-X.

Thus, the invention further provides the isolated genes operatively linked to a promoter of RNA transcription, as well as other regulatory sequences for replication and/or transient or stable expression of the DNA. To minimize chance of RCR it is preferred to avoid using MMLV LTR The term "operatively linked" is defined above.

The promoter is preferably "heterologous" to the retroviral gene. Suitable promoters are those that drive stable, high-level expression of gag-pol and env. Examples of suitable promoters include, but are not limited to, the cytomegalovirus immediate early (CMV) promoter, Rous Sarcoma Virus (RSV), or other viral LTR sequences. Vectors and plasmids which contain a promoter or a promoter/enhancer, with termination codons and selectable marker sequences, as well as a cloning site into which an inserted piece of DNA can be operatively linked to that promoter are well known in the art and commercially available. It is essential however, that the gag-pol and env genes be incorporated into separate expression plasmids. In plasmid amplification, the bacterial host cells containing the gag-pol and env gene expression plasmids are propagated at temperatures in the range from about 28° C. to about 32° C., and more preferably at about 30° C., prevents recombination of the viral sequences.

The separate expression plasmids containing the retroviral gag-pol and env genes are then introduced in separate, sequential steps into the candidate packaging cells by techniques well known to those of skill in the art, such as calcium phosphate precipitation, electroporation and transfection (Sambrook et al. (1989) supra). The insertion technique also can involve the use of a modified integrase enzyme that will recognize a specific site on the target cell genome. Such-site specific insertion allows the genes to be inserted at sites on host cells' DNA that will minimize the chances of insertional mutagenesis, minimize interference from other host cellular sequences, and allow insertion of sequences at specific target sites so as to reduce or eliminate the expression of undesirable genes.

Introduction of gag-pol and env can be done in either order. After insertion and integration of the gag, pol and env genes, the cells are screened for retroviral gene expression. If a selectable marker gene, such as antibiotic resistance, was used in combination with the retroviral sequences, the cells can be screened for expression of the selectable marker (and therefore the retroviral genes) by growing the candidate cells in the presence of the antibiotic. Cells which survive and propagate will contain both the antibiotic resistance gene and the retroviral sequences. Still further, a simple ELISA with the appropriate antibody to the viral proteins will be a simple and quick assay to determine whether and to what extent the cells contain and express the retroviral genes.

This invention also provides recombinant packaging cells obtained by the method described above. The recombinant packaging cell lines are an improvement over prior art packaging cell lines because, when transduced with a suitable retroviral vector and propagated, the cell lines of this invention produce a retroviral titer having high transduction efficiency. Thus, the cell line of this invention is characterized by producing viral supernatant that is resistant to human complement; has a high transduction efficiency; and is substantially free of RCR after continuous culture of more than 2 weeks and up to at least 8 weeks. As used herein, high transduction efficiency shall mean a recombinant retrovirus preparation (e.g., supernatant or supernatant concentrate) in which the number of active, transducing retroviral particles is increased relative to transduction inhibitors. Packaging cells of the present invention are able to produce recombinant retroviral supernatants of higher transduction efficiency than standard murine, PA317 cells as assayed on NIH/3T3 cells and particularly as assayed on human 293 or primary cells. Suitable reagents and methods for performing this analysis is provided in the experimental section below.

Also provided herein is a method of producing retroviral vector supernatant comprising transducing the novel packaging cells produced according to the method described above with a suitable retroviral vector to generate producer cells. This invention further provides the retroviral supernatant so produced. In addition to the gene of interest to be delivered to the host cell, the retroviral vector will contain the "packaging signal" that allows the retroviral vector nucleic acid to be packaged in the virus particle in the recombinant packaging cell line, and the long terminal repeat that allow the vector nucleic acid to become effectively integrated into the target cell genome. The LTRs are positioned at either end of the proviral nucleic acid and also generally contain regulatory sequences such as promoter/enhancers that affect expression of the therapeutic or marker gene of interest. The gene or genes of interest also can be operably linked to a suitable promoter which can be constitutive, cell-type specific, stage-specific and/or modulable. Enhancers, such as those from other virus, can also be included.

In a separate embodiment, the retroviral vectors can contain genes coding for selectable and/or detectable markers that facilitate isolation of transduced cells. In other embodiments, it may be desirable for the vector to include a "suicide gene" that allows recipient cells to be selectively eliminated at will. Isolation, insertion and use of such markers and suicide genes are well known to those of skill in the art as exemplified in PCT Publication Nos. WO 92/08796 and WO 94/28143.

Prior art methods to improve gene transfer (transduction) efficiency with retroviral vectors often focused on increasing the end-point titer. The evidence presented herein does not support a correlation between end-point titer and transduction efficiency. The evidence presented herein also does not support the conclusion that increasing end-point titer necessarily increases transduction efficiency because non-transducing particles interfere with transducing virions and reduce transduction efficiency without reducing-end point titer. Indeed, the evidence shows that packaging cell line clones should be screened for ability to generate supernatant with high transduction efficiency rather than end-point titers.

This invention further provides a method of producing retroviral vector supernatant having high transduction efficiency and suitable for gene therapy, comprising culturing producer cells in a packed-bed bioreactor having a surface to volume ratio of about 5 to 50 $cm^2/ml$, culturing the producer cells population at a temperature of around 30° C. to about 35° C. and harvesting supernatant produced by said producer cells at such time as the transduction efficiency of the supernatant is optimal for a target cell, thereby obtaining a high transduction efficiency supernatant suitable for gene therapy. As used herein, a packed-bed bioreactor refers to a cell culture vessel comprising a bed matrix in which cells grow in a static, confined three-dimensional space. In one embodiment, the packed-bed bioreactor comprises a bed matrix constructed such that there is a negligible pressure drop across the bed. In a separate embodiment, the surface to volume ratio is from about 20 to about 30 $cm^2/ml$ and preferably about 24 $cm^2/ml$. It is intended that any retroviral producer cell can be utilized in this method. However, the producer cells derived from the packaging cell lines produced according to the above method are particularly suited for use in this method for obtaining vector supernatant. Such cells include, but are not limited to producer cells derived from PA317 cells or 293 cells.

After seeding, the cells can be continuously cultured at 37 or 32° C. Preferably, the cells initially are cultured at 37° C. until the cells grow to a density of at least $10^6$ cells/ml, and are thereafter cultured at 32° C.

Preferred embodiments for culturing the cells to produce retroviral vector supernatant can vary based on the parental cell type of the producer cells. For example, the time to harvest the retroviral supernatant to obtain optimal transduction efficiency will vary with the parental cell type of the producer cells. As used herein, high transduction efficiency refers to a retroviral supernatant preparation in which the ratio of active, transducing retroviral particles to of transduction inhibitors is increased. Optimal transduction efficiency for a retroviral supernatant refers to the highest ratio of active, transducing retroviral particles to inhibitors, obtained under the culture conditions tested. Transduction efficiency is measured by testing the ability of any given recombinant retrovirus preparation, e.g., supernatant concentrate, to transduce a target cell population (e.g, NIH/3T3 cells, 293 cells, primary cells).

Perfusion is performed in fed-batch mode or constant perfusion mode. Fed-batch mode refers to changing the culture media at specific time intervals. Constant perfusion mode refers to the culture mode where fresh media is introduced into the bioreactor at a given rate while spent media is removed. Constant perfusion mode is preferred. Perfusion rates can vary. A constant perfusion rate can be at a constant rate of about 1 to about 24 reactor volumes per day, preferably from about 3 to about 12 reactor volumes per day, and more preferably from about 3 to about 12 reactor volumes per day. In the most preferred embodiment, the perfusion rate is at a constant rate of about 4 reactor volumes per day. In the most preferred embodiment, the perfusion rate increases as the cell density increases. Cell density can be monitored by lactose production. glucose utilization, or preferably, by oxygen uptake rate.

Further provided by this invention is a method of producing retroviral supernatant having high transduction efficiency, by seeding non-murine derived producer cells in a packed-bed bioreactor having a surface to volume ratio of about 5 to about 50 $cm^2/ml$, culturing the cells at a temperature of about 30° C. to about 35° C. and then harvesting the supernatant produced by the cells as such time that the transduction efficiency is optimal for a target cell population, thereby producing high transduction efficiency retroviral supernatant. In one embodiment, the packed-bed bioreactor comprises a bed matrix constructed such that there is a negligible pressure drop across the bed. In a separate embodiment, the surface to volume ratio is from about 20 to about 30 $cm^2/ml$ and preferably about 24 $cm^2/ml$. It is intended that any retroviral producer cell can be utilized in this method. However, the producer cells derived from the packaging cell lines produced according to the above method are particularly suited for use in this method for obtaining vector supernatant. Such cells include, but are not limited to producer cells derived from HT1080 cells, D17cells and 293 cells.

After seeding, the cells can be continuously cultured at 37° C. or 32° C. Alternatively, the cells initially are cultured at 37° C. until the cells grow to produce a confluent monolayer, and are thereafter cultured at 32° C. Aeration conditions can vary and can be empirically determined for each producer cell. However, it has been noted that when the packed-bed bioreactor is aerated such that the culture media is maintained at about 10% to about 50% air saturation, higher transduction efficiency supernatants are obtained. More preferred is aeration conditions providing air saturation from about 20% to about 50%, and most preferably about 30% air saturation.

The disclosed method also can be utilized to produce retroviral vector supernatant having high transduction efficiency by seeding primate producer cells in a packed-bed bioreactor having a surface area to volume ratio of about 5 to about 50 $cm^2/ml$ and then culturing the producer cells under constant perfusion mode at temperature of about 30° C. to about 35° C., and then harvesting the supernatant produced by the cells at such time as the transduction efficiency is optimal for a target cell population.

When the producer cell is derived from a 293 cell, it is preferably to harvest the retroviral supernatant when the culture media's mean residence time in the reactor is about 8 hours, starting from the time the producer cells reached a cell density of at least $10^6$ cell per ml. It is shown below that when the producer cells are derived from PA317 cells, the supernatant is preferably harvested when the culture media's mean residence time in the reactor is about 3 or more hours, starting from the time the cells have reached a cell density of at least $10^6$ cells per ml. Mean residence time can be decreased as cell density increases.

Further provided by this invention is a method of producing retroviral supernatant having high transduction efficiency, by seeding human-derived producer cells in a packed-bed bioreactor having a surface to volume ratio of about 5 to about 50 $cm^2/ml$, culturing the cells at a temperature of about 30° C. to about 35° C. and then harvesting the supernatant produced by the cells at such time as the transduction efficiency is optimal to a target cell population, thereby producing high transduction efficiency retrovirus preparation. In one embodiment, the packed-bed bioreactor comprises a bed matrix such that there is a negligible pressure drop across the bed. In a separate embodiment, the surface to volume ratio is from about 20 to about 30 $cm^2/ml$ and preferably about 24 $cm^2/ml$. The cells can be continuously cultured at about 30 to about 35° C.; however, culturing the cells initially at 37° C. until the cells reach confluence and then lowering the temperature to 32° C. is shown to be optimal. It is conceived that any producer cell derived from a primate can produce high transduction efficiency supernatant when cultured under these conditions. Examples of a primate cell is the human-based 293 cells, ProPak-A and ProPak-X.

One of skill in the art can easily empirically determine the most suitable culture medium for the cells using commercially available medium and supplementing the medium as provided in the art. However, for clinical use, serum-free medium is preferred.

Similar to the supernatant production methods described above, the primate cells produce exceptionally high transduction efficiency supernatant when perfused at a rate of about 3 to about 12 reactor volumes per day with aeration of the reactor. Most preferred is a perfusion rate of about 4 reactor volumes per day. It has been noted that aeration of the reactor such that culture media is maintained around 10% to about 50% air saturation provides high transduction efficiency supernatant. More preferred is aeration providing air saturation from about 20% to about 50%, and most preferably about 30% air saturation.

When the method is practiced with human based producer cells containing MMLV-based retroviral vectors, the cells are seeded into a bioreactor having surface to volume ratio of about 5 to about 50 $cm^2/ml$ at a concentration of about 2 to about $3 \times 10^4$ cells/$cm^2$, and the bioreactoroperated under constant perfusion with aeration and at a temperature of about 37° C. The cells are allowed to grow until cell density of greater that $10^6$ cells/ml is reached, and then the temperature is decreased to about 32° C. Retroviral supernatant is then collected after an additional 8 to about 24 hours of incubation time. Human cells useful in this method include, but are not limited to those derived from 293 cells, HT 1080 cells, ProPak-A cells and ProPak-X cells.

Reactor volume size can vary depending on the quantity of retroviral supernatant desired. Generally, the bed material will be one that supports the growth of anchorage-dependent cells. Preferably, the bed matrix is constructed such that there is a large void fraction thereby providing a negligible pressure drop across the bed. The negligible pressure drop ensures that media nutrients are well distributed to the cells across the bed during culture.

The culture supernatant produced by the methods described herein also is within the scope of this invention. The supernatant has been shown to transduce cells, and in particular, stem cells very efficiently.

Prior to transduction, the stem cells are isolated and selected. Methods of isolating and selecting cells are well known in the art. For example, sorted $CD34^+Thy1^+Lin^-$ cells from either adult bone marrow (ABM) or mobilized peripheral blood (MPB) are used. $CD34^+Thy1^+Lin^-$ are highly enriched in human hematopoietic stem cells. U.S. Pat. No. 5,061,620.

For the purposes of illustrating the preparation of ABM, fresh 20 mL of bone marrow can be isolated by aspiration of the iliac crest from normal human volunteers. Marrow is separated by taking the mononuclear cell fraction following a Ficoll-Perque separation, positive-selected for CD34+ cells according to the method described by Sutherland et al. (1992) Exp. *Hematol.* 20:590. Briefly, cells are resuspended in staining buffer (SB) (HBSS containing 10 mM HEPES, 2% heat-inactivated FCS) at $5 \times 10^7$ cells/mL. QBEND10 (anti-CD34) (Amac, Westbrook, Me.) is added at 1/100 dilution, and then the cells are incubated on ice for 30 min. Cells are then washed in SB with a FCS underlay, and resuspended at $4 \times 10^7$/mL in SB. An equal volume of washed Dynal sheep antimouse IgG Fc magnetic beads (Dynal, Oslo, Norway), is added at a 1:1 bead to cell ratio, to give a final cell concentration of $2 \times 10^7$ cells/mL. After 30 min incubation on ice, with gentle inversion, the tube was placed against a Dynal magnet (Dynal) for 2 minutes, and CD34− cells removed. Following two washes, 20 mL of 'glycoprotease' (O-sialoglycoprotein endopeptidase, Accurate Chemical, Westbury, N.Y.) plus 180 mL of RPMI (JRH Biosciences)/20% FCS is added and the beads incubated at 37° C. for 30 min to cleave the QBEND10 epitope, and release CD34+ cells from the beads. Beads are then washed three times to maximize cell recovery. The glycoprotease used for the release step in the positive selection procedure has been shown not to effect subsequent ex vivo expansion of progenitors. Marsh et al. (1992) *Leukemia* 6:926.

Mobilized peripheral blood (MPB) samples can be obtained with informed consent from multiple myeloma patients. Patients are treated on day 1 with cyclophosphamide at 6 g/m² (1.5 g/m² every 3 hours×4 doses). From day 1 until the start of leukopheresis (usually 10–28 days), granulocyte macrophage colony stimulating factor (GM-CSF) is given at 0.25 mg/m²/day. Apheresis for total white cells was started when the peripheral blood white cell count was greater than 500 cells/ml and the platelet count was greater than 50,000 cells/ml. Patients are apheresed daily until from $6 \times 10^8$ mononuclear cells (MNC) are collected.

Fresh MPB samples are then elutriated with a JE5.0 Beckman counterflow elutriator equipped with a Sanderson chamber (Beckman, Palo Alto, Calif.). Cells are resuspended in elutriation medium (Biowhittaker, Walkersville, Md.) at pH 7.2, supplemented with 0.5% human serum albumin (HSA). The rotor speed is set at 2000 RPM, the cells are introduced, and the first fraction collected at a flow rate of 9.6 ml/min. Fractions 2 and 3 are collected at the respective flow rates of 14 and 16 ml/min. The larger cells remaining in the chamber are collected after stopping the rotor. Cells are resuspended in RPMI supplemented with 5% HSA, 10 mg/ml DNAse I and penicillin/streptomycin at 50 U/ml and 50 mg/ml, respectively. Fractions 2 and 3 are pooled and incubated with 1 mg/ml heat-inactivated human gammaglobulin to block non-specific Fc binding. Granulocytes are further depleted by incubation with CD15 conjugated to magnetic beads (Dynal M450, Oslo, Norway) followed by magnetic selection.

CD34+Thy1+Lin− cells are isolated from ABM and MPB by flow cytometry as follows. Antibodies to CD14 and CD15 were obtained as FITC conjugates from Becton-Dickinson. Antibodis to Thy-1 (GM201) can be obtained from a commercial source or prepared and detected with anti-IgG1-PE conjugate from Caltag. Antibody to CD34 (T uk 3) also can be commercially obtained and detected with an anti-IGg3-Texas Red conjugate (Southern Biotechnologies).

Anti-CD34 antibody or an IgG3 isotype matched control is added to cells in staining buffer (HBSS, 2% FCS, 10 mM HEPES) for 20 minutes on ice, together with anti-Thy-1 antibody at 5 μg/ml. Cells are washed with a FCS underlay, and then incubated with Texas Red conjugated goat anti-mouse IgG3 antibody and phycoerythrin-conjugated goat anti-mouse IgG1 antibody for 20 minutes on ice. Blocking IgG1 is then added for 10 minutes. After blocking, the FITC-conjugated lineage antibody panel (CD14 and CD15) is added, and incubated for another 20 minutes on ice. After a final washing, cells were resuspended in staining buffer containing propidium iodide (PI).

Cells are sorted on a Vantage cell sorter (Becton Dickinson) equipped with dual argon ion lasers, the primary laser emitting at 488 nm and a dye laser (Rhodamine 6G) emitting at 600 nm (Coherent Innova 90, Santa Cruz, Calif.). Residual erythrocytes, debris and dead cells are excluded by light scatter gating plus an FL3 (PI) low gate. The sorted cell population was diluted 1:1 in HBSS, pelleted, and resuspended in HBSS for hemocytometer counting.

To transduce the cells, fresh or freshly thawed retroviral supernatant is diluted in appropriate media containing cytokines. Cells and virus are then centrifuged and resuspended and cultured in cytokine-enriched media for about three days. After three days, the cells are harvested and used to determine bulk transduction frequency as described below. Alternatively, the cells can be introduced into a patient by methods well known to those of skill in the art for gene therapy.

The following examples are intended to illustrate, not limit the scope of the invention disclosed herein.

Experimental

As noted above, successful retroviral-mediated gene therapy requires safe and efficient packaging cell lines for vector particle production. Existing packaging lines for murine leukemia virus-based vectors are predominantly derived from NIH/3T3 cells which carry endogenous murine viral sequences which could participate in recombination to form replication competent retrovirus (RCR), thereby rendering them unsafe. Provided herein are methods for obtaining safe and efficient retroviral packaging cell lines for vector particle production as well as the cell lines so obtained.

Materials and Methods

Unless otherwise stated, materials and reagents are prepared and methods are conducted, as set forth below. Producer cell lines are named by noting the packaging cell line and inserted vector. For example, PA-SVNLZ denotes a producer cell line derived from packaging cell line PA317 transfected with vector SVNLZ PPA and PPX denote ProPak-A and ProPak-X, respectively.

PA317-Based Cell Lines and Retroviral Vectors

The virus producer cell lines disclosed herein were generated from the amphotropic PA317 packaging cell line produced according to the methods of Miller and Buttimore, (1986) Mol. Cell Biol. 6:2895–2902. Producer cell lines, the GP+E86 packaging cell line produced according to the method of Markowitz, et al. (1988) *J. Virol.* 62:1120–1124, and NIH/3T3 cells (ATCC CRL1658) were cultured in Dulbecco's modified Eagle medium (DMEM) supplemented with 4.5 g/L of glucose, 4 mM L-glutamine and 5% Cosmic Calf Serum (CCS, Hyclone, UT). The human epithelial carcinoma line HeLa (ATCC CCL2) was cultured in DMEM supplemented with 4.5 g/L of glucose, 4 mM L-glutamine and 10% fetal bovine serum (FBS, Hyclone, UT). The human lymphoid cell line Jurkat was cultured in RPMI supplemented with 4.5 g/L of glucose, 2 mM L-glutamine, and 10% FBS. All cell lines were maintained in an incubator at 37° C. under 5% CO2 unless otherwise stated.

The SVNLZ (see Bonnerot, et al. (1987) *Proc. Natl. Acad. Sci. U.S.A.* 84:6795–6799) and LMTNL vectors are known in the art. (See for example, Escaich et al. (1995) *Human Gene Therapy* 6:625–634) FIG. 2 sets forth a map of these vectors. The SVNLZ vector encodes the LacZ gene with a nuclear localization signal expressed from the simian virus 40 early promoter (FIG. 2). The LMTNL vector encodes a trans-dominant mutant of the HIV Rev protein (RevM10) expressed from the MMLV-LTR, and the neomycin phosphotransferase (neo) gene expressed from the thymidine kinase promoter (FIG. 2).

PA317 Culture Conditions

For virus production, PA317-based producer cells were seeded into culture vessels at a density of $3 \times 10^4$ cells/cm$^2$ unless otherwise noted. Once the cells had formed a confluent monolayer (approximately 3 days), the medium was changed and the temperature lowered from 37° C. to 32° C. For virus production, three types of culture vessels were used: (1) 75-cm tissue culture flasks with filter caps (Costar, Cambridge, Mass.); (2) 900-cm$^2$ roller bottles with filter caps (Costar, Cambridge, Mass.); or (3) a 500 ml bench scale packed-bed bioreactor (New Brunswick Scientific, Edison, N.J.) with 10 g of Fibra Cell discs (12,000 cm$^2$). Samples from the bioreactor (1 ml) were removed with a sterile syringe through a sampling port. Supernatant samples were cleared of cellular debris by filtration through 0.45 μm nitrocellulose filters (Nalgene, Rochester, N.Y.), snap-frozen in methanol/dry-ice, and stored at −70° C. Frozen supernatants were thawed at 37° C. and kept on ice until assayed. All supernatants used in this study were free of replication competent retrovirus as determined by the S+L- assay on PG4 cells as described in Cornetta, et al. (1993) *Human Gene Therapy* 4:579–588.

Assays for Retroviral Vectors

LacZ end-point titration

NIH/3T3 cells were plated into 24 well plates at $5 \times 10^4$ cells per well, and inoculated the next day with 0.2 ml of diluted vector supernatant ($10^{-1}$ to $10^{-6}$ dilution series) in the presence of polybrene (8 μg/ml). Three hours after inoculation, the inoculum was aspirated and 0.5 ml of fresh medium added. Three days post inoculation, the cells were fixed with 0.5% glutaraldehyde and stained with X-gal using the protocol of Bagnis et al. (1993) *Oncogene* 8:737–743. The end-point titer (cfu/ml) was calculated by counting a statistically representative number of blue colonies in a well, multiplied by the dilution factor, and divided by the volume of the inoculum. All end-point titrations were performed in duplicate.

For the xenotropic vectors prepared using ProPak-X, titrations were performed using the same procedure except that human 293 cells were used as the target cells.

LacZ transduction efficiency

Cells were plated into 24 well plates at $5 \times 10^4$ cells per well, and inoculated the next day with 0.2 ml of a 1:1 dilution of vector supernatant with medium in the presence of polybrene (8 μg/ml). Three hours after inoculation, the inoculum was aspirated and 0.5 ml of fresh medium added. Transduction efficiencies were determined three days post-inoculation by flow cytometry using the FluoReporter lacZ detection kit (Molecular Probes, Inc., Eugene, Oreg.). For NIH/3T3 or 293 cells, the reaction with fluorescein di-β-D-galactopyranoside (FDG) was quenched after one minute with 1 mM phenethylthio-β-D-galactopyranoside (PETG). For Jurkat and HeLa cells, PETG was added after a one hour incubation on ice. Acquisition and analysis were performed using a Becton Dickinson FACScan and the LYSYS software package. Transduction efficiency was determined as the percentage of cells expressing the lacZ gene (green fluorescence intensity) above the basal fluorescence levels set by non-transduced control cells.

G418 resistance end-point titer

Titrations were performed in 6 well plates seeded at $2.5 \times 10^4$ NIH/3T3 cells per well, and inoculated the next day with 1.0 ml of diluted vector supernatant ($10^{-1}$ to $10^{-6}$ dilution series). Three hours after inoculation, the inoculum was aspirated and 2.0 ml of fresh medium was added. One day after inoculation, G418 was added to each well at a final concentration of 0.7 mg/ml, and the medium was changed as required until individual colonies could be seen (typically 10 to 14 days). The end-point titer (cfu/ml), was calculated by counting a statistically representative number of G418 resistant colonies in a well and multiplied by the dilution factor.

For the xenotropic vectors prepared using ProPak-X, titrations were performed using the same procedure except that human 293 cells were used as the target cells.

G418 resistance transduction efficiency

Cells were seeded into 6 well plates at $1 \times 10^5$ cells per well. The next day, cells were inoculated with 1.0 ml of a 1:1 dilution of vector supernatant with medium in the presence of polybrene (8 μg/ml). Three hours after inoculation, the inoculum was aspirated and 2.0 ml of fresh medium was added. Three days post-inoculation, adherent cells were trypsinized and seeded into 6 well plates at a 10-fold dilution series from $10^5$ cells/well to 1 cell/well. Jurkat cells were plated in methylcellulose to allow individual colonies to be scored. Duplicate plates were seeded, and incubated in the presence or absence of G418. The percentage transduction efficiency was calculated as the number of G418-resistant colonies divided by the number of colonies that formed in the absence of G418, multiplied by 100.

EXAMPLE 1

Construction of Packaging Cells

To minimize the chance of recombination with endogenous viral sequences to form RCR, candidate cell lines were screened for endogenous retroviral, and in particular, endogenous MMLV nucleic acids. Genomic DNA from a variety of cell lines was analyzed by Southern blot hybridization by the method generally disclosed in Sambrook et al., (1989) *Molecular Cloning: A Laboratory Manual* 2nd ed., Cold Spring Harbor Laboratory, New York, using probes specific to retrovirus MMLV long terminal repeat (LTR) or MMLV gag-pol sequences. The following cell lines were screened: COS cells which are used to produce recombinant proteins (Hodgson, (1993) *Bio/Tech.* 11:887–890); Vero and MRC-5 cells in which vaccines are produced (WHO (1989) "*Technical Report Series No. 786*" WHO, Geneva), and human embryonic kidney 293 cells (ATCC CRL 1573) that are used to produce adenovirus vectors for clinical gene therapy applications and retroviral vectors (Pear et al. (1993) *Proc. Natl. Acad. Sci. U.S.A.* 90:8392–8396; Finer et al. (1994) *Blood* 83:43–50). *Mus dunni* tail fibroblasts (NIH) also were included since these cells are reportedly free of endogenous MMLV sequences (Lander and Chattopadhyay (1984) *J. Virol.* 53:695–698). Genomic DNA from NIH/3T3 cells, the basis for the majority of existing packaging cell lines, hybridized very strongly with both MMLV-specific probes at low or high stringency. Hybridization conditions are provided in the figure legend below the table appearing in FIG. 13. Consistent with a previous report (Lander and Chattopadhyay (1984) supra). Strong hybridization also was seen with CHO-K1 cell DNA under high hybridization conditions. In contrast, neither probe cross-hybridized with genomic DNA from 293 or MRC-5 cells, even at low stringency (Table 1). In addition, no cross-hybridization was seen with genomic DNA from *Mus dunni*, MDCK, Vero or Fox Lung cells at high-stringency (see Table 1, below).

TABLE 1

Screening of cell lines for cross-hybridization to MMLV LTR or gag-pol sequences.
Endogenous MMLV Sequences (Hybridization)

| | Hybridization Probe: | | | |
|---|---|---|---|---|
| | LTR | | gag/pol | |
| | Wash Stringency: | | | |
| Cell Lines Tested | Low | High | Low | High |
| 293 (ATCC CRL 1573) | – | – | – | – |
| MDCK (ATCC CCL 34) | ± | – | ± | – |
| *Mus dunni* tail fibroblasts | ± | – | ± | – |
| Vero (ATCC CCL 81) | – | – | ± | – |
| Fox Lung (ATCC CCL 168) | – | – | ± | – |
| MRC-5 (ATCC CCL 171) | – | – | – | – |
| NIH/3T3 (ATCC CRL 1658) | ++ | ++ | ++ | ++ |
| CHO-K1 (ATCC 61) | ++ | ++ | ++ | ++ |

Key:
Hybridization signal strength: –, none; ±, weak; +, moderate; ++, strong.
Probes: LTR (positions relative to cap site of genomic RNA): nucleotides –232 (Eco RV) to 563 (Pst I of 5' leader sequence); gag-pol: nucleotides 739 (Pst I in gag) to 3705 (Sal I in pol).
Stringency (65° C. in all instances): Low, 500 mM Na+; High, 50 mM Na+.
ATCC: American Type Culture Collection, 12301 Parklawn Drive, Rockville, Maryland, 20852, U.S.A.

Fox Lung and MRC-5 were discounted due to poor growth or limited cell division potential respectively, which would preclude sub-cloning of stably-transfected cells. Thus, 293, MDCK, *Mus dunni* and Vero cells were identified as candidate cell lines from which to derive packaging cell lines.

To decrease the probability of RCR formation, separate expression plasmids were constructed for gag-pol and env, as disclosed in Danos (1991) *Proc. Natl. Acad. Sci. U.S.A.* 85:6460–6464; Danos and Mulligan, (1988) *Proc. Natl. Acad. Sci. U.S.A.* 85:6460–6464; Markovitz et al. (1988) *J. Virol.* 62:1120–1124; Miller (1990) *Human Gene Therapy* 1:5–14; Morgenstern and Land (1990) *Nucl. Acids Res.* 18:3587–3596. In contrast to existing packaging cells, however, only the minimum genetic information required to encode gag-pol and env proteins was included. The structural gene sequences were amplified by polymerase chain reaction (PCR) to obtain the open reading frames (ORFs) from the initiation to the termination codons of the gag-pol or env genes flanked by Not I restriction sites, and the fragments were subcloned into pBluescript SK+ (Stratagene, La Jolla, Calif.). Oligonucleotide primers (Genosys Biotechnologies, Woodlands, Tex.) corresponding to the N-terminus of the genes also placed the AUG in the ideal context for translation (Kozak (1987)) *J. Mol. Biol.* 196:947–950), and those corresponding to the C-terminus encoded a second in-frame stop codon. The gag-pol ORF was amplified from the plasmid pVH-2, which carries the infectious Moloney MMLV sequence (Miller and Verma (1984) *J. Virol.* 49:214–222), using the primer pair:

5'-AAAAAAAAGCGGCCGCGCCGCCACC ATGGGCCAGACTGTTACCAC-3' (SEQ ID NO. 1), and
5'-AAAAAAAAGCGGCCGCTCAttaGGGGGCCTC GCGGG-3' (SEQ ID NO.2).

The underlined ATG is that of the p15Gag (bases 621 to 623) and the codon in lower case corresponds to the pol stop codon (bases 5835 to 5837). The expression plasmid pCMV-gp with the human cytomegalovirus immediate early (CMV) promoter was constructed by inserting the gag-pol fragment into the pcDNA3 plasmid (Invitrogen, San Diego, Calif.) from which the neomycin resistance expression cassette (DraIII to BsmI) had been deleted. FIG. 1 schematically shows the plasmid constructs used for expression of MMLV structural genes. Plasmids carrying the gag-pol ORF were propagated at 30° C. to prevent recombination under the conditions set forth in Joshi and Jeang (1993) *BioTechniques* 14:883–886. To amplify the env gene, a contiguous amphotropic envelope sequence was constructed from p4070A constructed according to the method of Ott et al. (1990) *J. Virol.* 64:757–766, and amplified with the primer pair:

5'-TAATCTACGCGGCCGCCACCATGGCGCGTTCAA CGCTC-3' (SEQ ID NO. 3)
and
5'-AATGTGATGCGGCCGCtcaTGGCTCGTACTCTA TGG-3' (SEQ ID NO. 4)

The underlined ATG corresponds to bases 37 to 39, and the stop codon (lower case), bases 1998 to 2000 (Ott et al. (1990) supra. The CMV promoter-env expression plasmid pCMV*Ea was created by insertion of the env ORF in place of the beta-galactosidase gene of pCMVB (Clontech, Palo Alto, Calif.) modified by mutation of an extraneous ATG in the SV40 intron to ACG. The integrity of the PCR products was verified by DNA sequencing.

To further identify the optimal cell line, sandwich ELISA assays were developed to detect gag and env proteins in transfected cells and supernatants. Plates were coated with hybridoma culture supernatants from either 83A25 (available from the NIH) as disclosed in Evans et al. (1990) *J. Virol.* 64:6176–6183, for env, or R187 (ATCC CRL 1912) for gag. Captured proteins were detected with 79S-834 and 77S-227 anti-sera (Quality Biotech, Camden, N.J.), respectively, and horseradish peroxidase-conjugated anti-species antibodies and 2,2-Azinobis (3-ethylbenzothiazoline-6-sulfonic acid) (Pierce, Rockford, Ill.). The ability to produce vector particles was assessed by transfection of a gag-pol expression plasmid into candidate cell lines and selection of drug-resistant pools. Only the supernatants from gag-pol -transfected 293 or *Mus dunni* cells contained gag protein. No gag was secreted by transfected Vero or MDCK cells, although gag was present in the cell lysates. Vero and MDCK cells were discounted as candidate cell lines:, and human 293 cells were elected to derive packaging cells.

Construction of ProPak-A

To derive amphotropic packaging cells, the pCMV*Ea plasmid was introduced (env) into 293 cells (ATCC CRL 1573) by co-transfection (Profection Kit, Promega, Madison, Wisconsin) at a ratio of 15:1 with the pHA58 plasmid (as disclosed in Riele et al. (1990) *Nature* 348:649–651) conferring resistance to hygromycin B (250 mg/ml; Boehringer, Indianapolis, Id.). Stably-selected populations were stained with anti-env antibody (83A25, available from the NIH) and individual env-positive cells were isolated by automatic cell deposition on a FACStar Plus (Becton Dickinson, San Jose, Calif.). Three clones with the highest fluorescence intensity were further characterized. All three yielded equivalent titers upon transient co-transfection with gag-pol and vector plasmids.

Next, the pCMV-gp construct was stably transfected into one of the three 293-env clones by cotransfection with the plasmid pSV2pac (as disclosed in Vara et al. (1986) *Nucl. Acids Res.* 14:4617–4624). Puromycin-resistant (1 mg/ml; Sigma, St. Louis, Mo.) clones were grown to confluence, medium was exchanged and supernatants were collected 16 hours later, filtered, and analyzed for gag and env production by ELISA. Sixteen (16) clones were identified (16/37) that secreted high levels of gag and env antigens. Of these, six clones produced virus in transient transfections at titers within 2 to 3-fold of Oz 2 cells (Table 2A), the amphotropic equivalent of BOSC 23 cells (see Pear et al. (1993) *Proc. Natl. Acad. Sci. U.S.A.* 90:8392–8396).

TABLE 2A

Comparison of end-point titers from transiently-transfected ProPak-A cell clones

| Transient Titers-<br>MFG lac Z Vector<br>Cell Line or<br>Clone # | End-Point Titer<br>(cfu × $10^{-5}$/ml) |
|---|---|
| Oz 2 | 13.8 ± 0.3 |
| ProPak.12 | 8.8 ± 0.8 |
| ProPak.31 | 8.0 ± 0.5 |
| ProPak.6 | 7.5 ± 0.0 |
| ProPak.27 | 6.8 ± 1.2 |
| ProPak.21 | 6.0 ± 1.0 |
| ProPak.5 | 6.0 ± 2.0 |

Supernatants were collected after 16 hours at 32° C., and end-point titers determined on NIH/3T3 cells using the materials and methods disclosed above. cfu: colony forming units. Cells were seeded at 2×$10^5$ cells/cm$^2$ in 6-well plates, and transfected 16 hours later with 2.5 mg/well MFG-lacZ DNA (Dranoff et al. (1993) supra and described herein) was in the presence of 25 mM chloroquine (Pear et al. (1993), supra). Titers are the average and range for duplicate transfections. Oz 2 cells also are called Bing cells.

TABLE 2B

Comparison of end-point titers from transiently-transfected stable producer cell clones with the LMTNL Vector
End-Point Titer

| Producer Clone | (G418$^r$ cfu × $10^{-6}$/ml) |
|---|---|
| PA317.LMTNL | 1.7 ± 0.7 |
| ProPak-A.6.LMTNL.6 | 2.1 ± 0.3 |
| ProPak-A.6.LMTNL.7 | 2.2 ± 0.8 |

Supernatants were collected after 16 hours at 32° C., and end-point titers determined on NIH/3T3 cells
cfu: colony forming units.
Supernatants were harvested from confluent cultures of producer cell clones in T-75 flasks. The average and range for triplicate samples is given.

One clone with high transient transfection titers was selected and designated ProPak-A.6 This clone was deposited with the American Type Culture Collection (ATCC), 12301 Parklawn Drive, Rockville, Md. 20852 U.S.A. on Dec. 15, 1995, under the provisions for the Budapest Treaty for the Deposit of Microorganisms for the Purposes of Patent Procedure. The deposit was accorded ATCC Accession No. CRL 12006 Transient titers reflect the efficiency of transient transfection, and the titers obtained with ProPak-A cells are lower than those achieved with Oz 2 cells, possibly because Oz 2 is based on a 293T cell clone selected for high transient transfection efficiency (Pear et al. (1993) supra).

Construction of ProPak-X

A xenotropic packaging cell line, designated ProPak-X, was constructed as follows. The ATG in the splice donor/splice acceptor of pCMV plasmid was mutated to ACG as described above. The CMV promoter was excised (EcoR1/XhoI, blunt-ended), and replaced with the MMLV LTR (Asp 718/HindIII, blunt-ended) from plasmid pVH2. The β-galactosidase gene was replaced by the gag-pol ORF (NotI fragment) to generate pMMLVgp. pMMLVgp was co-transfected with pHA58 into 293 cells (ATCC CRL 1573) by calcium phosphate co-precipitation and hygromycin β-resistant cells were selected. Clones were screened for the level of gag secretion and one clone secreting high levels of gag was selected and yielded high viral titers in transient transfection (designated pro-gag).

The plasmid pNZBxeno, containing the murine xenotropic env gene, was obtained from Christine Kozak NIH). The non-contiguous env sequences in pNZBxeno were made contiguous by digestion with SalI and EcoRI and ligation into the SalI site of pBluescript (Stratagene). The xeno env ORF was amplified by PCR and cloned into XhoI/XbaI digested pCI (Promega) to generate the expression plasmid pCI*Ex. pCI*Ex was co-transfected with pSV2pac into the cell line selected as above (pro-gag) by calcium phosphate precipitation and puromycin-resistant cells were selected. The resulting cells were screened for env expression as described above, and one clone designated ProPak-X.36, expressing high levels of env was further selected. Samples of the cell (clone) have been deposited with the American Type Culture Collection (ATCC), 12301 Parklawn Drive, Rockville, Md. 20852 U.S.A. on Dec. 15, 1995, under the provisions for the Budapest Treaty for the Deposit of Microorganisms for the Purposes of Patent Procedure. The deposit of ProPak-X.36 was accorded ATCC Accession No. CRL 12007

Supernatant produced by ProPak-X based producer cells were tested for end-point titer and transduction efficiency as described above, except that human 293 cells were used as the target cells.

Lack of RCR

The safety of the ProPak-A cells was determined by stringent testing for the ability to recombine to generate RCR. In previous work it was found that the vector BC140revM10 (Bevec et al. (1992) *Proc. Natl. Acad. Sci. U.S.A.* 89:9870–9874) reproducibly gave rise to RCR in PA317 cells. BC140revM10 carries the extended packaging sequence, including the ATG of the gag ORF. The LMTNL vector (constructed as described in Escaich et al. (1995) supra), in contrast, lacks part of the 5' untranslated region and contains no gag sequences and is therefore less likely to recombine and form RCR. (See FIG. 2). The BC140revM10 or LMTNL vectors were each introduced into PA317 or ProPak-A cells and culture supernatants were tested for RCR (using the methods disclosed in Haapala et al. (1985) *J. Virol.* 53:827–833 and Printz et al. (1995) Gene Therapy 2:143–150) at weekly intervals. The PA317/BC140revM10 combination (transfected or transduced) gave rise to RCR detectable by direct inoculation of culture supernatant onto PG4 cells at 4 weeks (Table 3, below). Cultures were maintained for 4 more weeks, and also tested by co-culture of producer cells with *M. dunni* cells to amplify any RCR in the culture, followed by S+L-assay on PG4 cells. Even by this stringent assay for RCR, the ProPak-A-based producer pools were all free of RCR (Table 3).

TABLE 3

Assay for presence of RCR in cultures carrying the BC140revM10 or LMTNL vectors

| Packaging Cell Line | Transfected with: | Transduced with: | Supernatant RCR (wk) | Co-culture RCR (wk 8) |
|---|---|---|---|---|
| ProPak-A | pBC140revM10 | N/A | (>8) | Negative |
| ProPak-A | pLMTNL | N/A | (>8) | Negative |
| ProPak-A | N/A | M(G).BC140revM10 | (>8) | Negative |
| ProPak-A | N/A | M(G).LMTNL | (>8) | Negative |
| PA317 | pBC140revM10 | N/A | 4 | Not tested |
| PA317 | pLMTNL | N/A | (>8) | Negative |
| PA317 | N/A | M(G).BC140revM10 | 4 | Positive |
| PA317 | N/A | M(G).LMTNL | (>8) | Negative |

RCR detected by S + L- assay on PG4 cells (ATCC CRL 2032) by inoculation with supernatant from producer cell cultures, or after 3 passages of co-culture with *Mus dunni* cells.
N/A: not applicable.
(>8): no RCR detected 8 weeks after G418-resistant pools established.
M(G).: transient MMLV(VSV-G) pseudotype (Yee et al.(1994) Proc. Natl. Acad. Sci. 91:9564–9568) used as inoculum.

Resistance to inactivation by human serum

Figure 10:
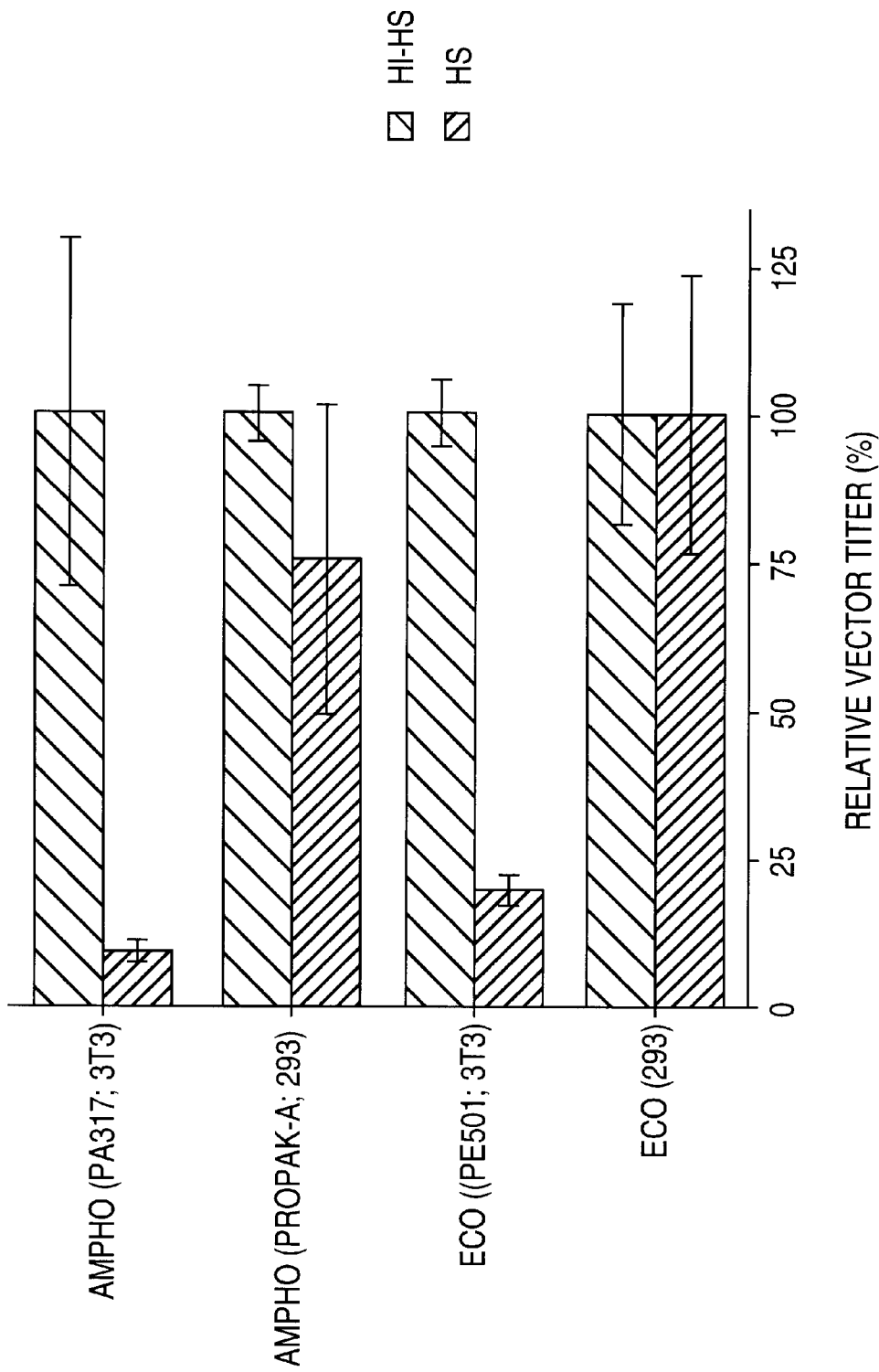
FIG. 10 shows the result of lacZ-encoding vector supernatants were prepared from stable producer cells (PA317; PE501), by transient transfection of vector into packaging cells (ProPak-A) or by co-transfection of packaging and vector constructs into 293 cells (293). Supernatants were mixed with an equal volume of a pool of human serum from 4 healthy donors, incubated for 1 hour at 37° C., and the residual titer determined on NIH/3T3 cells by the method of Takeuchi et al. (1994). *J. Virol.* 68:8001. The serum was either untreated (HS) or had been heat-inactivated for 30 min at 56° C. (HI-HS). The human serum pool had a hemolytic titer (CH50; EZ Complement Assay, Diamedix, Miami, Fla.) of 117 to 244 before, and <8 after heat-inactivation. End-point titers (cfu×10–5/ml) of supernatants treated with heat-inactivated serum (100%) were: PA317, 5.0; ProPak-A, 1.0; PE501, 1.4, and 293, 1.1. The bars indicate the range for duplicate samples. HI-HS denotes heatinactivated human serum. HS denotes human serum.

Recently, interest has arisen in the In vivo application of retroviral gene transfer by direct administration of vector particles into human beings. In addition, targeting of particles bearing hybrid ligand-ecotropic env to specific receptors has been reported (Kasahara et al. (1994); *Science* 266:1373–1376 Somia et al. (1995); *Proc. Natl. Acad Sci. U.S.A.* 92:7570–7574; Cosset et al. (1995) *J. Virol.* 69:6314–6322). A pre-requisite is that the particles are not inactivated by human serum. Therefore, the susceptibility of ProPak-A- or PA317-packaged vector particles was analyzed for susceptibility to inactivation by human serum. In addition ecotropic supernatants packaged in either PE501 cells NIH/3T3-based; see Miller and Rosman, (1989) *BioTechniques* 7:980–990 or in 293 cells were analyzed. Vector particles with either envelope produced from 293 cells were resistant, while supernatants packaged in NIH/3T3 cells were inactivated by incubation with human serum (FIG. 10). Takeuchi et al. (1994) supra, concluded that resistance of vector particles to human serum was determined by both the host cell type and the viral envelope. The data submitted herein shows that packaging of amphotropic and ecotropic vectors in 293-based cells is sufficient to confer resistance to human complement.

For the data presented in Examples 2 and 3, herein, the parental packaging cell line was PA317, unless otherwise noted.

EXAMPLE 2

Comparison of End-Point Titer and Transduction Efficiency

For gene therapy applications, it is necessary to generate large volumes of characterized supernatants, which cannot be easily prepared by transient transfection.

It was therefore necessary to determine the stable end-point titers and the transduction efficiencies. End-point titers were determined for supernatants from producer cell clones which had been transduced with the LMTNL vector, in which an internal thymidine kinase promoter (T in vector name) drives the neomycin phosphotransferase gene (N). End-point titers from ProPak-A-based producer cells were marginally higher than those for our best PA317-based producer clone. In addition, the titers from ProPak-A.LMTNL producer pools were stable when passaged for 3 months in the absence of drug selection.

Figure 9A:
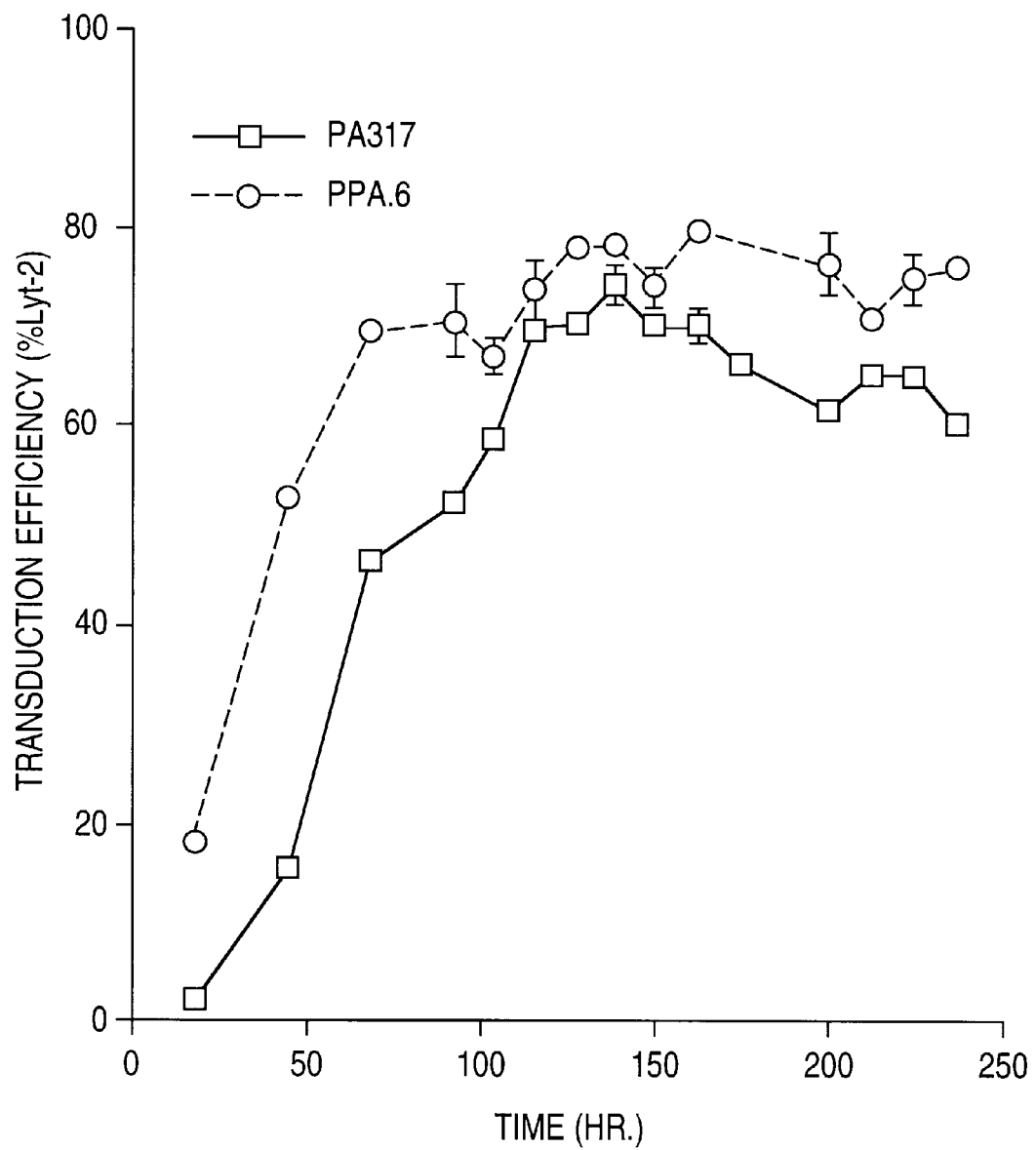
FIG. 9A is a comparison of viral supernatant transduction efficiency produced from ProPak-A and PA317 cells as on NIH/3T3 cells.
Figure 9B:
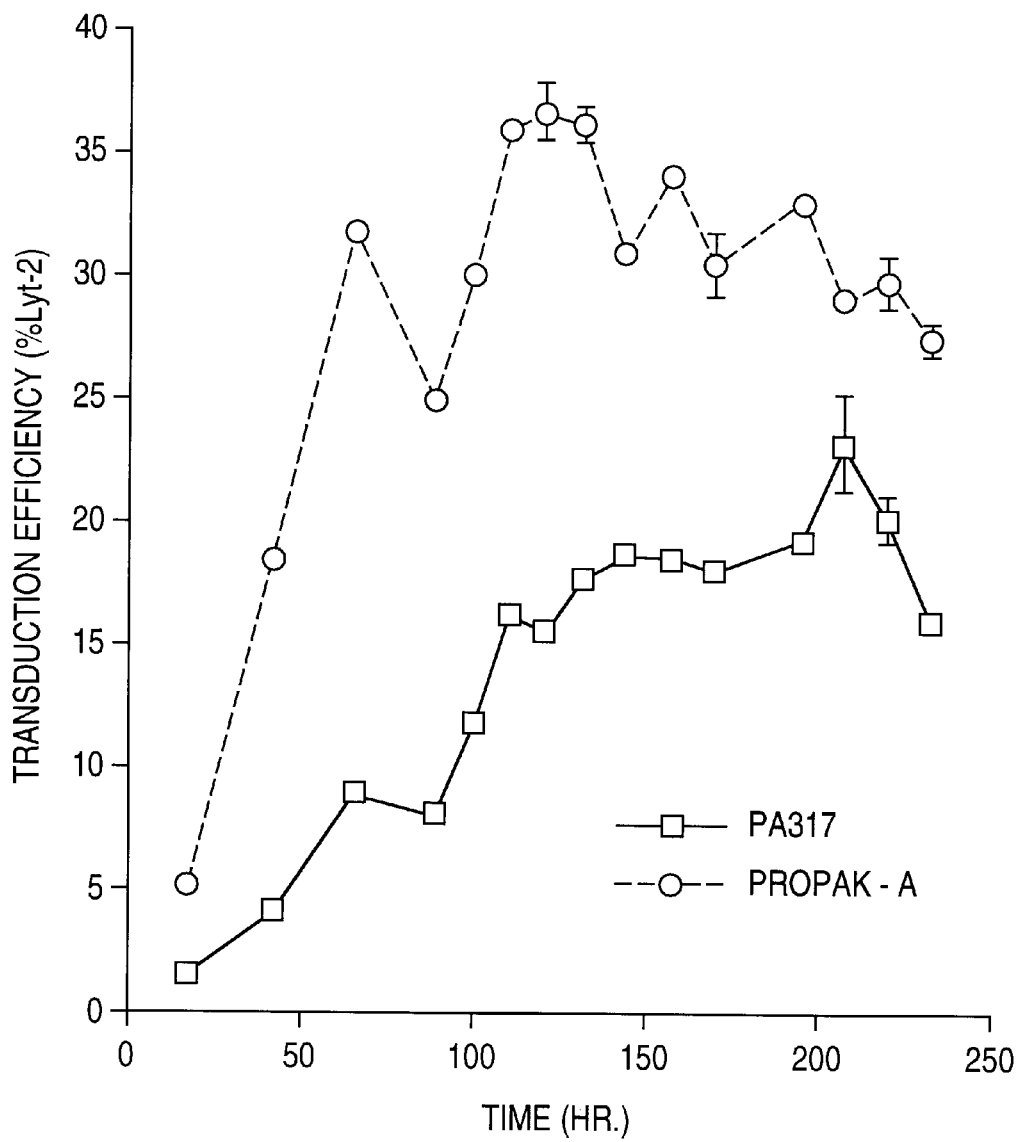
FIG. 9B is a comparison of viral supernatant transduction efficiency produced from ProPak-A and PA317 in an aerated packed-bed bio-reactor.
Figure 9C:
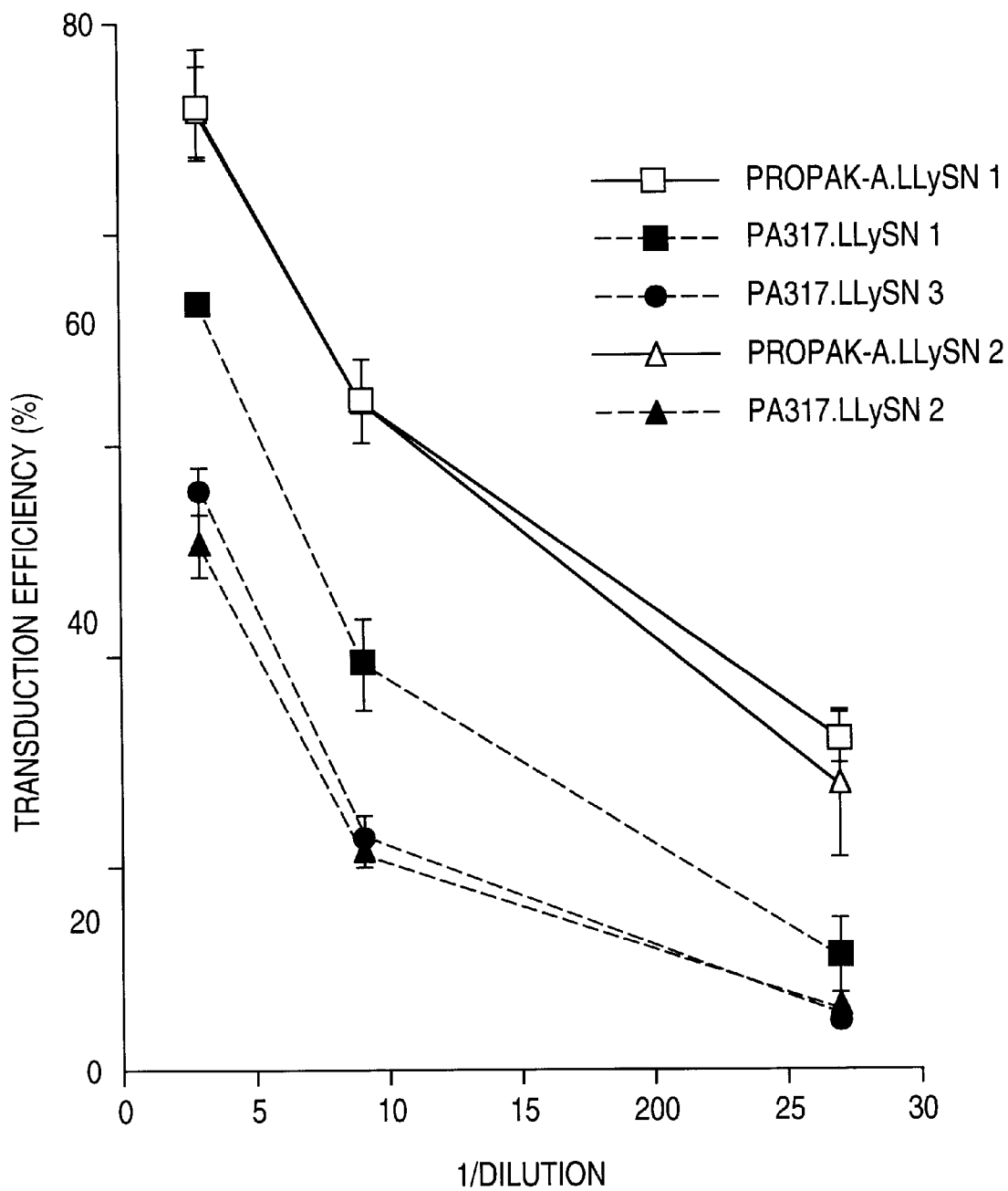
FIG. 9C show quantification of the transduction efficiencies was achieved with Lyt2-encoding (LLySN) vector supernatants from PA317 or ProPak-A-based producer cells as the proportion (%) of NIH/3T3 cells that stained (FACScan, Becton Dickinson) with anti-Lyt2 antibody (Pharmingen, San Diego, Calif. 2 days after inoculation with the dilutions of vector supernatant shown. Supernatants were prepared from confluent producer cell cultures after 12 hours at 32° C.

As shown herein, while end-point titers are broadly used, transduction efficiency is a better measure of gene transfer potency. However, the assay can be laborious with vectors encoding drug resistance genes. Therefore PA317- or ProPak-A-based producer cell populations carrying a vector (LLySN, FIG. 2) derived from the LXSN vector (Miller and Rosman (1989) supra) were prepared by insertion of the Lyt2 surface marker gene (Tagawa et al. (1986) supra). Surface expression of the Lyt2 antigen allows simple, quantitative determination of transduction efficiency by FACS. Higher transduction efficiencies were achieved with supernatants from two independently-derived ProPak-A-LLySN populations than with supernatants from three PA317.LLySN pools assayed on NIH/3T3 cells (see FIG. 9A). Surprisingly, when the same supernatants were assayed for transduction efficiency on human 293 cells, the superiority of ProPak-A is even greater (FIG. 9B).

Figure 3A:
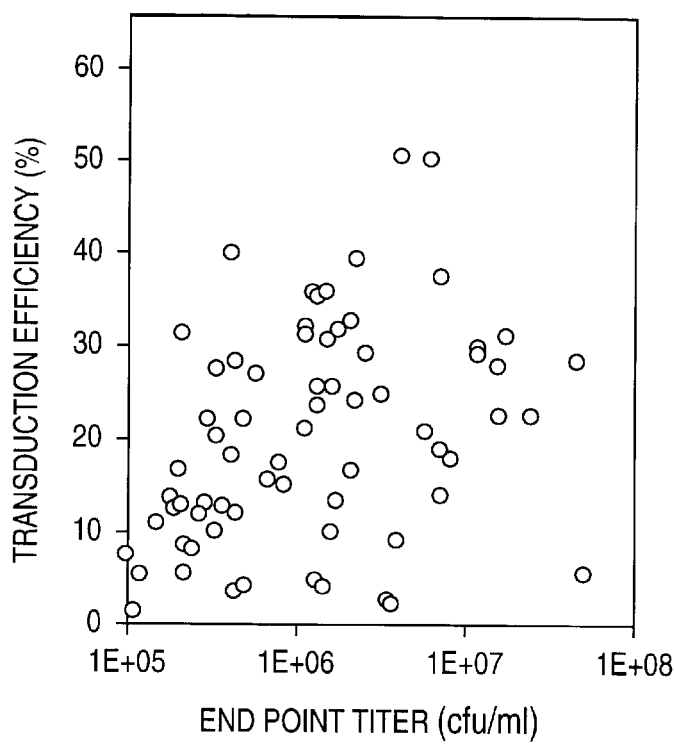
FIGS. 3A and 3B show the results of comparison of viral vectors.
Figure 3B:
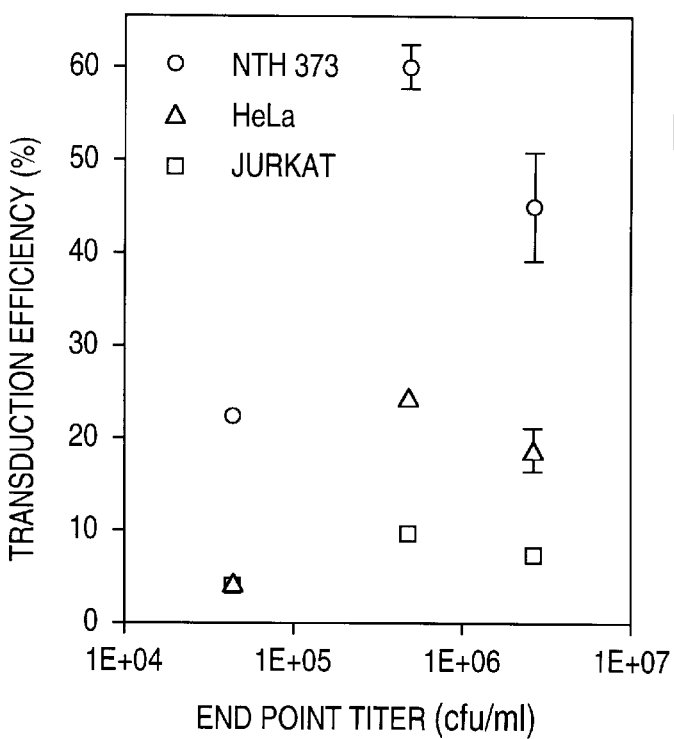

To determine the relationship of end-point titer to transduction efficiency, supernatants were harvested from producer cells cultured under a variety of conditions to optimize production of retroviral vector supernatants. In addition to assaying end-point titers, the proportion of cells transduced after a single inoculation (i.e. transduction efficiency) also was determined. FIG. 3A shows the end-point titers and transduction efficiencies obtained with 70 different PA317-derived -β-galactosidase-encoding SVNLZ (PA-SVNLZ; FIG. 2A) vector supernatants. No direct correlation between the end-point titer and transduction efficiency of the supernatants was found (correlation factor, r =0.07). To confirm that the lack of correlation between transduction efficiency and end-point titer was not specific to the NIH/3T3 cells or the flow cytometry method used to quantitate the proportion of cells transduced with the PA317-derived SVNLZ vector, supernatants containing an amphotropic retrovirus encoding the neomycin phosphotransferase gene (LMTNL, FIG. 2) were tested on NIH/3T3 as well as Jurkat and HeLa cells (FIG. 2). The results demonstrate that the supernatant which yielded the highest transduction efficiency on NIH/3T3 cells also gave the highest transduction efficiency on both Jurkat and HeLa cells (FIG. 3B). Furthermore, the supernatant which yielded the highest transduction efficiency did not have the highest end-point titer, again distinguishing between these two functional measurements. Similar results also were obtained with the SVNLZ vector on several different cell lines suggesting that the lack of correlation between end-point titer and transduction efficiency is neither specific to the indicator gene nor to the target cell species.

Concentration of Vector Supernatants

The lack of correlation between end-point titer and transduction efficiency also was apparent when the effect of physically concentrating retroviral vector supernatants by ultrafiltration was examined. Vector supernatants were concentrated using three different ultrafiltration systems. The Sartocon Mini cross flow ultrafiltration system (Sartorius, Bohemia, N.Y.) was used with a 77.4 $cm^2$, 100,000 kDa molecular weight cut-off (MWCO) polysulfone module at a feed pressure of 3 pounds per square inch (psi). Concentration was achieved within one hour at room temperature. An Amicon Stirred Cell model 8050 (Amicon, Beverly, Mass.) was used with a YM100 ultrafilter (3.4 cm$^2$, 100,000 kDa MWCO). Positive-pressure was maintained with sterile, filtered regulated air, and concentration achieved in 30 minutes at room temperature. Small volumes (5 to 20 ml), were concentrated using Filtron 300,000 kDa MWCO centrifugal concentrators (Filtron Tech. Corp., Northborough, Mass.). Concentration was achieved within 45 minutes by centrifugation at 3,000 g in a Beckman GS-6KR centrifuge (Beckman, Palo Alto, Calif.) at 4° C.

Figure 4:
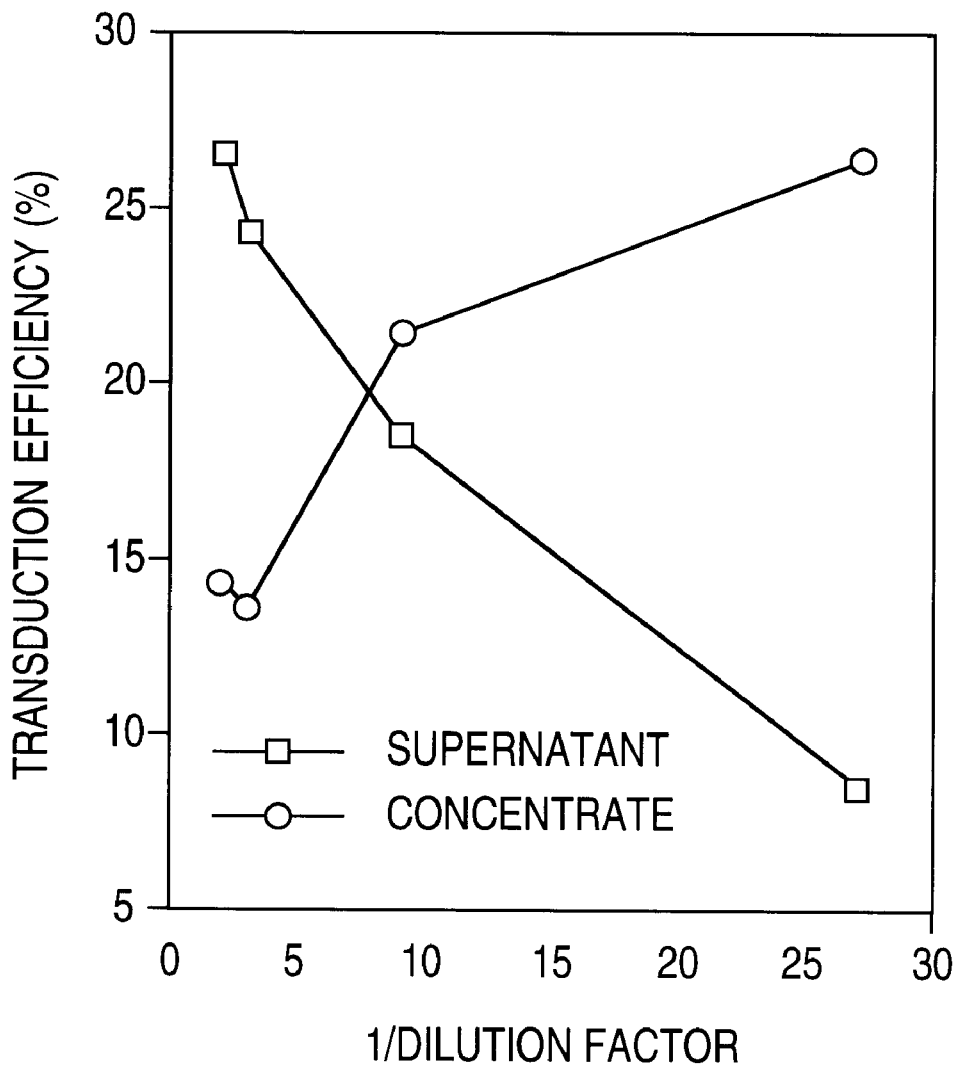
FIG. 4 shows the transduction efficiency of SVNLZ supernatants before or after concentration. The original supernatant and the concentrate (see Experiment 2 and FIG. 13) were diluted with medium and inoculated onto NIH/3T3 cells.

FIG. 13 summarizes data from five independent experiments using two different retroviral vectors and the three different ultrafiltration systems. End-point titers increased in proportion to the volume reduction (up to 19-fold), indicating that the virus was not inactivated by this procedure. However, higher transduction efficiencies were not achieved. Equivalent transduction efficiencies were achieved with supernatants produced at 32° C. before and after concentration (FIG. 13). In contrast, retroviral vector supernatants produced at 37° C. had lower transduction efficiencies following ultrafiltration (FIG. 13). Interestingly, the lower transduction efficiencies could be restored to the level of the original supernatant by diluting the concentrates (see FIG. 4), suggesting that an inhibiting agent had been co-concentrated with the transducing virus particles. In principle, the inhibitor could be non-transducing retroviral particles, non-virus-associated envelope protein, or a non-viral component of the tissue culture supernatant.

Envelope-Specific Inhibition of Retroviral Vector Transduction

To address the nature of the inhibiting agent, tissue culture supernatant from different packaging cell lines or NIH/3T3 cells was tested to determine whether it could inhibit transduction. Supernatants from packaging cell lines contain all the necessary viral particle proteins, but lack vector genomes and hence are unable to transduce cells. Ecotropic vectors use different receptors to enter cells than amphotropic vectors and competition for binding to receptors can occur only between viral particles with the same tropism. PA-SVNLZ supernatant was mixed with supernatant from the following: parental amphotropic PA317 packaging cells; supernatant from the ecotropic GP+E86 packaging cell line; PA-SVNLZ concentrate from above or supernatant from NIH/3T3 cells, and the transduction efficiency and end-point titers were measured.

Addition of supernatant from NIH/3T3 cells or the GPE+86 packaging cell line had no effect on transduction efficiency or end-point titer (Table 4). In contrast, addition of either parental PA317 or concentrated derived producer cell line PA-SVNLZ vector supernatant reduced transduction efficiency, even though in the latter case, the end-point titer was increased by addition of the concentrated PA-SVNLZ supernatant (Table 4). These data indicate that the inhibition is specific to the amphotropic envelope protein in particulate or free form.

TABLE 4

Comparison of the transduction of NIH/3T3 cells achieved with PA.SVNLZ supernatant diluted 1:1 with other supernatants.

| Supernatant | Transduction† Efficiency (%) | End-Point† Titer (cfu/ml × 10$^6$) |
|---|---|---|
| NIH/3T3 | 22.9 ± 0.5 | 1.4 ± 0.5 |
| GP + E86 (no vector) | 24.0 ± 0.5 | 2.0 ± 0.3 |

TABLE 4-continued

Comparison of the transduction of NIH/3T3 cells achieved with PA.SVNLZ supernatant diluted 1:1 with other supernatants.

| Supernatant | Transduction† Efficiency (%) | End-Point† Titer (cfu/ml × 10$^6$) |
|---|---|---|
| PA317 (no vector) | 12.1 ± 0.4 | 2.5 ± 0.3 |
| Conc. PA-SVNLZ* | 12.7 ± 0.4 | 3.7 ± 0.1 |

*8.4-fold concentrate with Sartocon 100 kD ultrafilter (Experiment 1, FIG. 13)
†values given are the average of two samples, and the range.

Stability of Retroviral Vectors at Different Temperatures

Figure 5A:
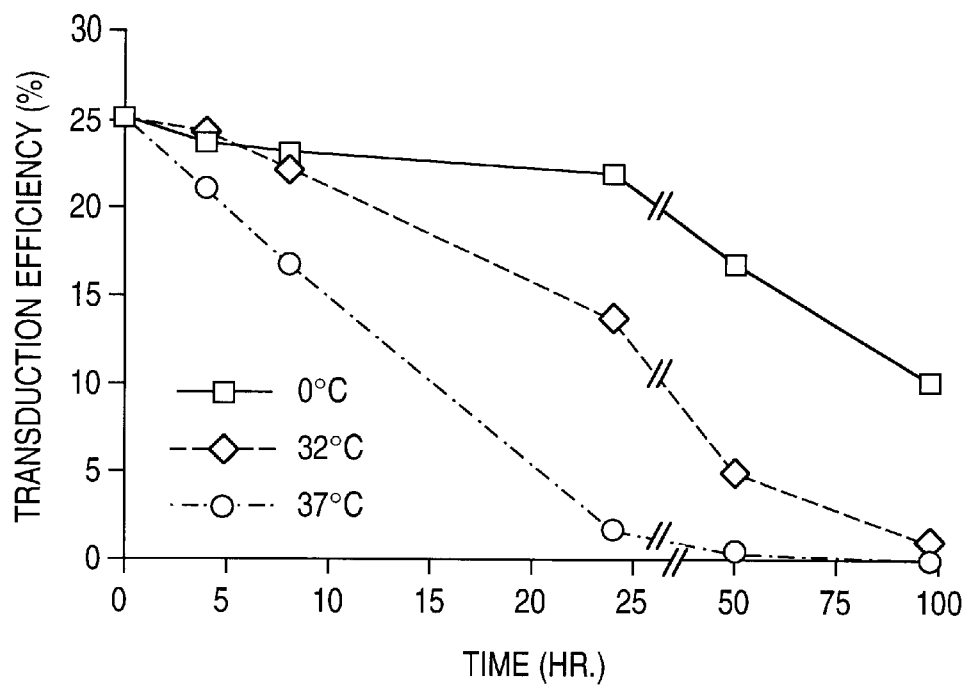
FIGS. 5A and 5B are a measurement of transduction efficiency (FIG. 5A) or end-point titer of SVNLZ retroviral vector supernatant on NIH/3T3 cells (FIG. 5B), showing the inactivation of vector incubated at 37° C., 32° C. or 0° C. IE+05 means a dilution of $1\times10^{-5}$, IE+06 means a dilution of $1\times10^{-6}$, etc.
Figure 5B:
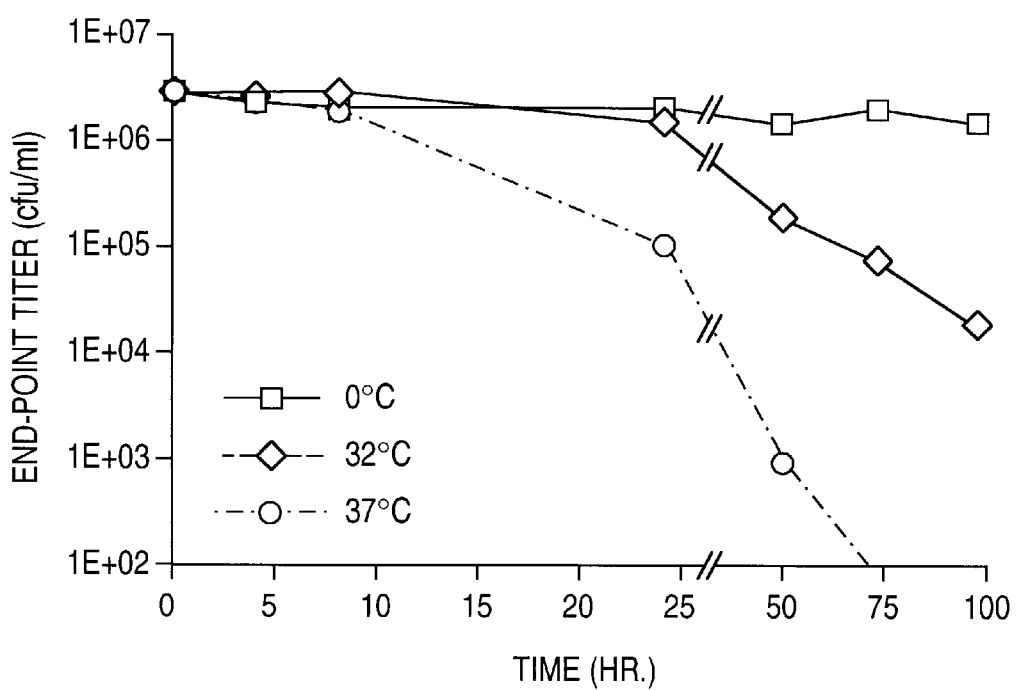

Concentration of supernatant produced at 37° C. reduced transduction efficiency relative to the original supernatant (FIG. 13). It is possible that these supernatants contain a higher proportion of inactivated virus than supernatants produced at 32° C. To test retroviral particle stability at different temperatures, SVNLZ supernatant produced at 32° C. was incubated at either 37° C., 32° C., or 0° C. for various lengths of time. The original supernatant had a transduction efficiency of 25% (see FIG. 5A), and after incubation for 24 hours at 37° C., 32° C. or 0° C. the transduction efficiencies were reduced to 2, 14 and 22% respectively. Incubation at 0° C. for 4 days further reduced the transduction efficiency to 12%, while the end-point titer remained relatively stable (see FIG. 5B). At all temperatures examined, transduction efficiency declined more rapidly than end-point titer. The half-life of virus particles at 37° C. was calculated as 4.1 hour based on the end-point titer, similar to previous reports. The half-life of virus at 32° C. and 0° C. was 12.0 hours and 123.4 hours, respectively. It is interesting to note that at all temperatures examined, end-point titer remained relatively stable (2.5±0.4×10$^6$ cfu/ml) for at least the first eight hours. This initial stability in end-point titer, which was not observed for transduction efficiency, has been seen in three separate experiments using either the PA-SVNLZ or PA-LMTNL vector.

Retroviral Production Kinetics

Figure 6A:
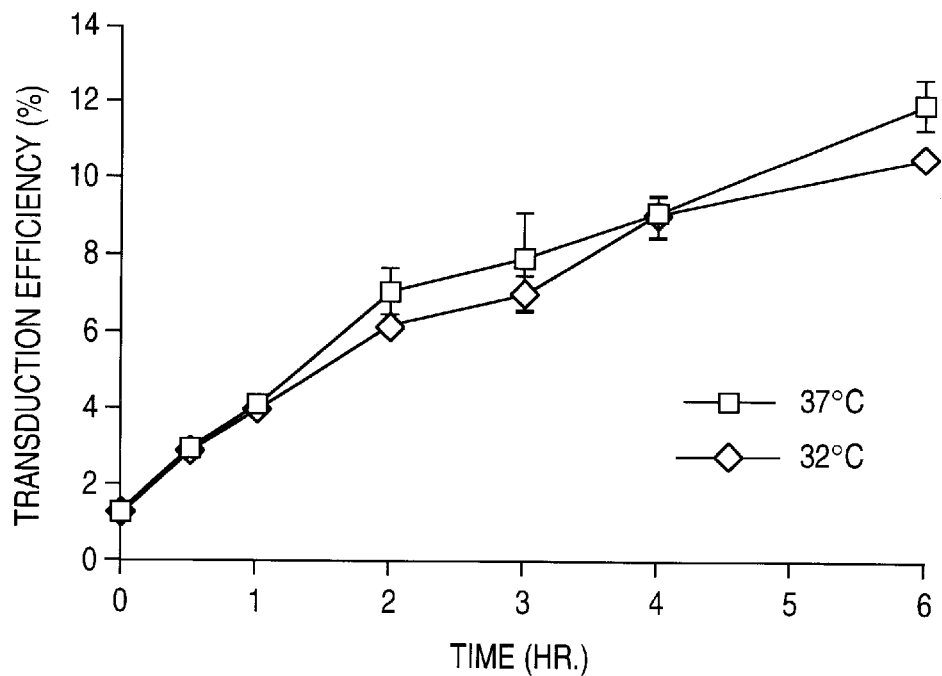
FIGS. 6A and 6B show a time-course of production of SVNLZ retroviral vector in a 75 cm² tissue culture flask at 32° C. or 37° C. measured as either transduction efficiency (FIG. 6A) or end-point titer on NIH/3T3 cells (FIG. 6B).
Figure 6B:
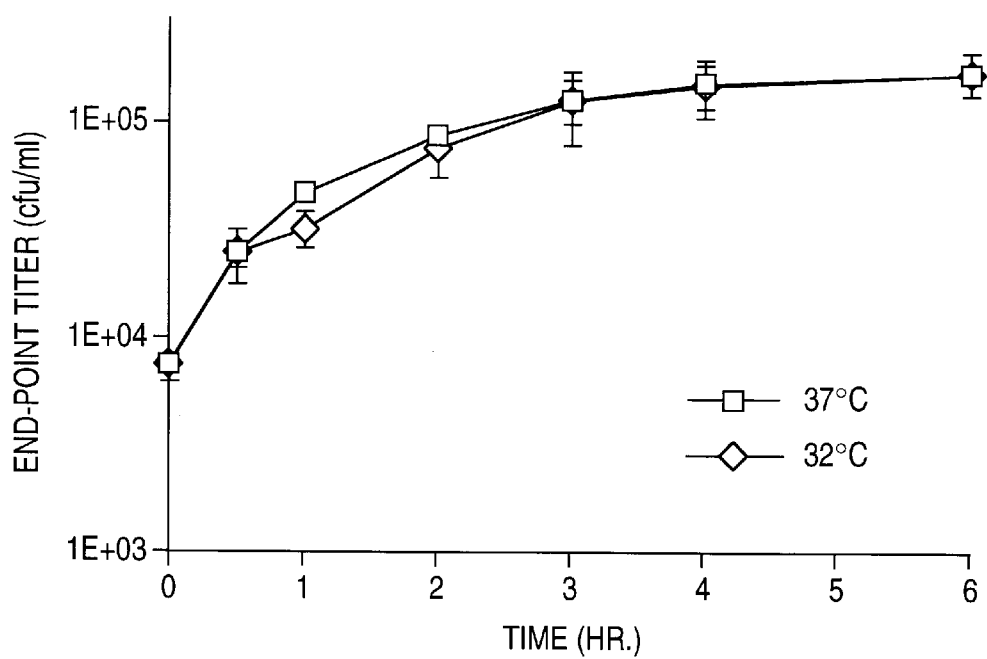

Given the greater stability of retroviral vector particles at 32° C. than at 37° C., experiments were performed to study the kinetics of virus production at these temperatures. SVNLZ producer cells were grown to approximately 80% confluency at 37° C., at which time the medium was changed and the cells placed at either 37° C. or 32° C. Supernatant samples were collected at different time points, snap-frozen, and assayed for both end-point titer (FIG. 6A) and transduction efficiency (FIG. 6B). Over the first 6 hours, similar amounts of transducing virus accumulated in cultures at 37° C. or 32° C. (FIGS. 6A and 6B). Calculations incorporating the inactivation rate of the virus at 37° C. or 32° C. show that the rate of virus production is slightly higher at 37° C. than at 32° C. (0.031 cfu/cell/hour compared to 0.027 cfu/cell/hour). Consistent with this, the amount of p30 capsid or gp70 envelope protein present in the samples measured by ELISA demonstrated that secreted viral protein production is also marginally higher at 37° C. than at 32° C. Similar results were also found with the LMTNL vector.

Figure 7:
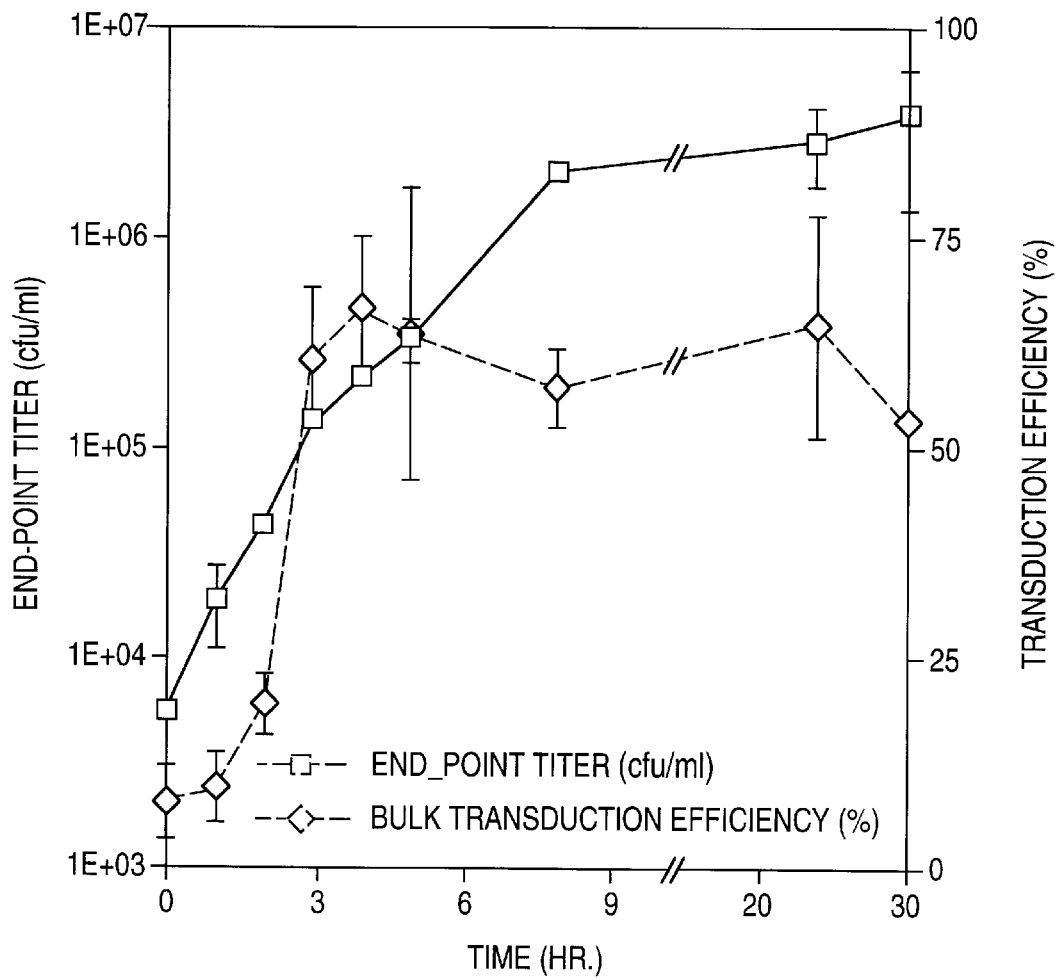
FIG. 7 is a time-course of LMTNL vector production from a confluent roller bottle culture at 32° C. as measured by transduction efficiency or end-point titer.

While the rate of virion inactivation is lower at 32° C. than 37° C., the inactivation of vector particles at 32° C. is still significant (FIG. 5A), and the time that supernatants remain at this temperature should therefore be minimized. Experiments were performed to determine the minimum time required to produce supernatants with maximal transduction efficiency. FIG. 7 gives the time-course of virus production from a confluent PA-LMTNL producer cell culture in a roller bottle at 32° C., and shows that the transduction efficiency reaches a plateau 3 hours after medium exchange.

EXAMPLE 3

Comparison of Production Methods

Figure 8A:
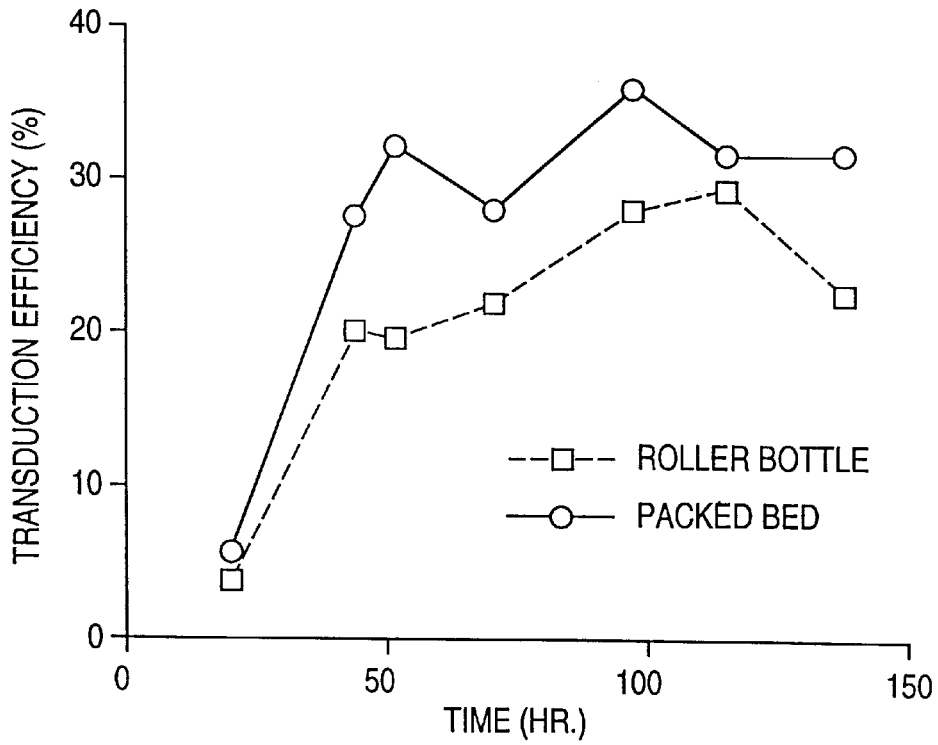
FIGS. 8A and 8B show a time-course of vector production for SVNLZ producer cultures in a roller bottle (900 cm²) or packed bed-bioreactor (12,000 cm²) shown by transduction efficiency (FIG. 8A) or end-point titer (FIG. 8B). IE+05 means a dilution of $1\times10^{-5}$, IE+06 means a dilution of $1\times10^{-6}$, etc.
Figure 8B:
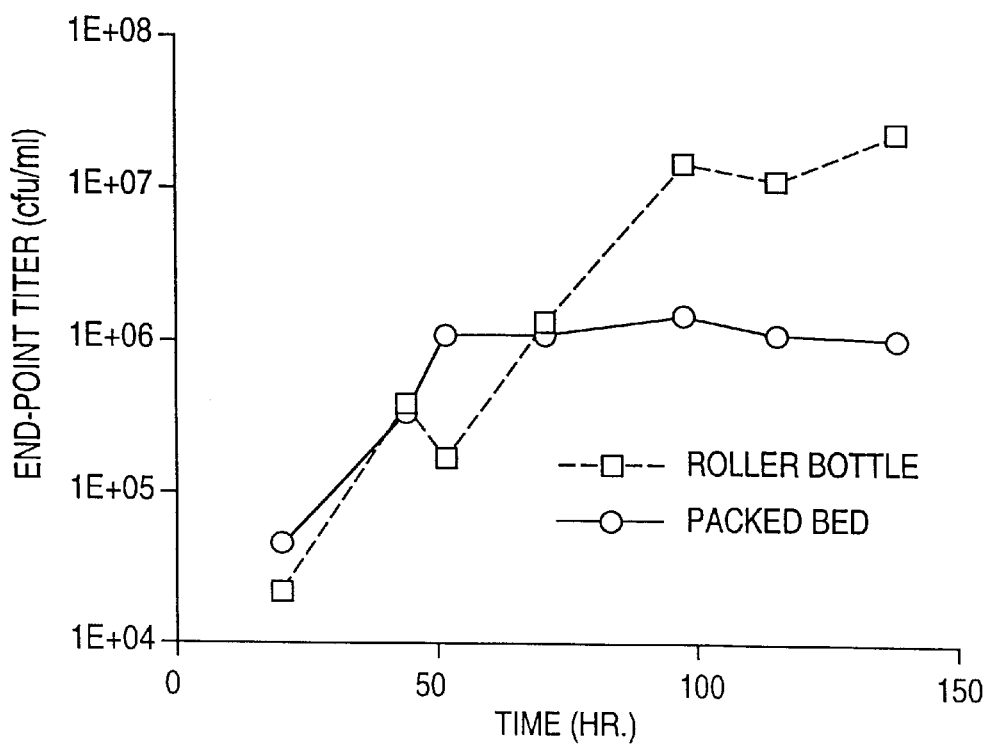

The kinetics of virus production from PA317-based producer cell lines suggest that once producer cells reach confluency, supernatants should be collected every 3 to 5 hours to obtain supernatant with a high transduction efficiency. To achieve these conditions, a bench scale packed-bed bioreactor was operated under either fed-batch (periodic medium exchange) or perfusion mode (continual medium perfusion). In the latter, supernatant leaving the bioreactor was collected into a container at 0° C. to minimize inactivation. Initial experiments with the PA-SVNLZ producer cell line cultured in the packed-bed bioreactor operated in fed-batch mode showed comparable virus production by end-point titer and transduction efficiency to that in tissue culture flasks. Next, the packed-bed bioreactor was operated in perfusion mode and compared to a roller bottle operated in fed-batch mode (Table 5). Sampling of supernatants from the bioreactor or roller bottles began one day after cells were seeded. In both cultures, incubation was initially at 37° C. and lowered to 32° C. after 50 hours. The cells in both cultivation systems reached confluency after approximately 100 hours of incubation. Transduction efficiencies achieved with supernatants produced in the packed-bed bioreactor were greater than those from roller bottle cultures (FIG. 8A). However, supernatants produced in the packed-bed bioreactor had lower end-point titers than supernatants from the roller bottle (FIG. 8B) due to the shorter residence time of the medium in the reactor (5.75 hours compared to 24 hours for the roller bottle). Over a 5 day period a total of 10 L of supernatant was collected using the packed-bed bioreactor, compared to 1 L from the roller bottle.

TABLE 5

Operating Parameters of Different Production Systems

| Parameter | Packed Bed Bioreactor* | Roller Bottle |
|---|---|---|
| Surface Area (cm$^2$) | 12,000 | 1,700 |
| Volume (ml) | 500 | 200 |
| Mode of Operation | perfusion | fed-batch |
| Dilution Rate (Vol./day) | 4.2 | 1.0 |
| Total Production Vol. (ml) | 10,000 | 1,000 |
| Seeding Density (cells/ml) | 6.5 × 10$^5$ | 2.3 × 10$^5$ |
| Final Density (cells/ml) | 5.91 × 10$^6$ | 9.06 × 10$^6$ |
| End-Point Titer (cfu/ml) | 1.45 × 10$^6$ | 2.40 × 10$^7$ |
| Transduction Efficiency (%) | 36.0 | 29.5 |

*10 g of Fibercell discs in bench-top New Brunswick Scientific bioreactor
Corning expanded surface area roller bottle

EXAMPLE 4

Comparison of Virus Production from ProPak-A and PA317 Cells Supernatant Production from Bioreactor 10 g of the New Brunswick Scientific Fiber Cell disks (catalog #M1176-9984) are placed into the spinner basket of the Packed-bed bioreactor (catalog #M1222-9990) and washed several times with PBS before autoclaving. Prior to inoculation, the bioreactor and Fibercell discs are washed 2× in medium with 5% FBS.

The reactor is inoculated with 2.4 to 3.6×10$^8$ producer cells (same for ProPak and Pa317) in a total volume of 500 ml of medium (i.e. 2 to 3×10$^4$ cells/cm ) (DMEM with 5% to 10% FBS). The agitation rate upon inoculation is set at approximately 80 rpm. A minimum of 3 hours is required for all of the cells to become attached to the Fibercell discs.

Figure 11:
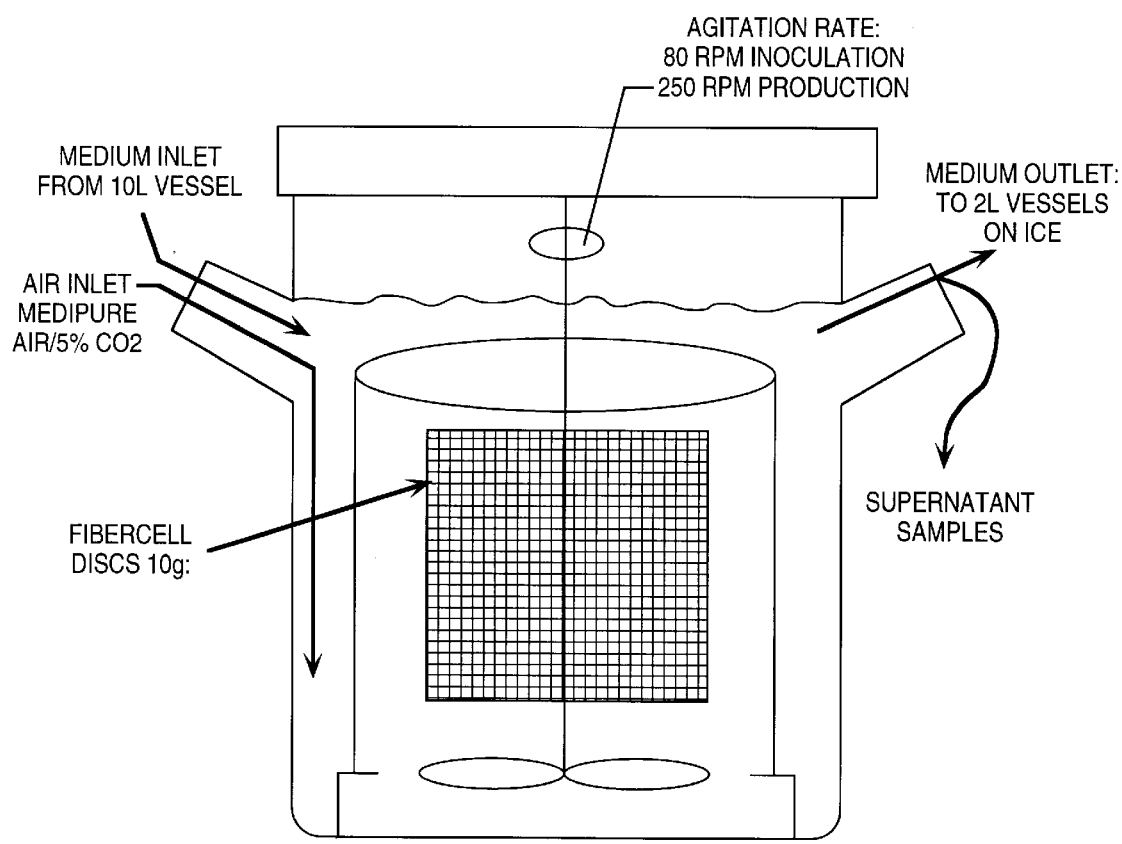
FIG. 11 illustrates a bioreactor that is suitable for the production of retroviral vector supernatant.
Figure 12:
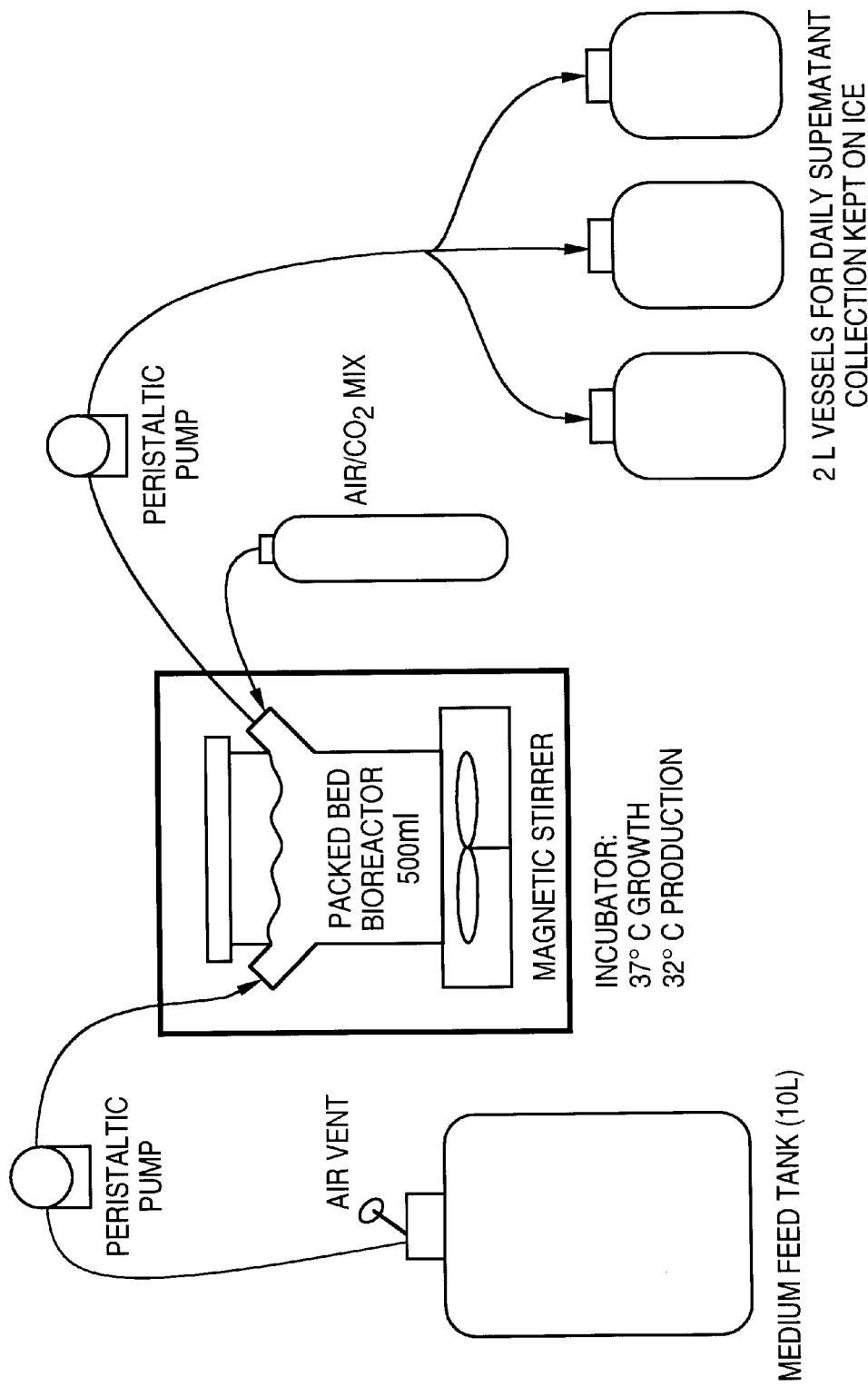
FIG. 12 illustrates the set up of a continuous perfusion bioreactor that is suitable for the production of retroviral supernatant.

Approximately 4 to 18 hours after inoculation, 50% of the medium is exchanged, and 5 ml of Pluronic F68 (Sigma cat#P5556) is added to the bioreactor to a final concentration of 0.1%. At this time aeration is initiated by gently sparging medical grade air/5% $CO_2$ mix (Altair cat#39222) into the reactor through a 0.2 mm filter. Agitation is increased to approximately 250 rpm. Cells are allowed to grow for three days at 37° C. and then the temperature is lowered to 32° C. Medium exchanges should be performed on the cells every 4 to 12 hours, or the reactor operated in perfusion-mode. Perfusion is at a rate of 0.7 to 2.1 ml/min (peristaltic pump is calibrated each time). Perfused supernatant harvested from the bioreactor is collected into 2 L glass vessels (vented cap) kept on ice. The harvested supernatant is filtered through a 0.45 μm filter, aliquoted, and snap frozen in MeOH/dry ice. The bioreactor and set-up of the continuous perfusion operation are shown in FIGS. 10 and 11.

Supernatant Preparation from Roller Bottles

Producer cells are seeded at 3×10$^4$ cells/cm$^2$ in 0.25 ml of DMEM plus 5% FBS per cm$^2$ of surface area. The rotational speed is set at 0.6 rpm. Cells are grown at 37° C. for two days. On day three the temperature is decreased to 32° C. The medium is aspirated and replaced with fresh DMEM medium plus 5% FCS (0.2 ml/cm$^2$ of surface area). Medium is added with a pipet to the bottom of the flask to prevent cells from peeling off and to avoied bubble formation and cell contact. The serum level may be lowered to 2% FBS.

For PA317-based producers, two batches of medium are collected every day (every 12 hours) and pooled to make a single lot. For ProPak-A based producers, supernatants are collected every 12 to 24 hours. Each batch is filtered through a 0.45 μm filter immediately, and kept at 4 C. until batches are pooled (approximately 12 hours). The pooled batches are aliquoted, snap frozen in MeOH/dry ice, and stored at −80° C. Supernatant collection can continue until the cells begin to peel off.

Figure 15:
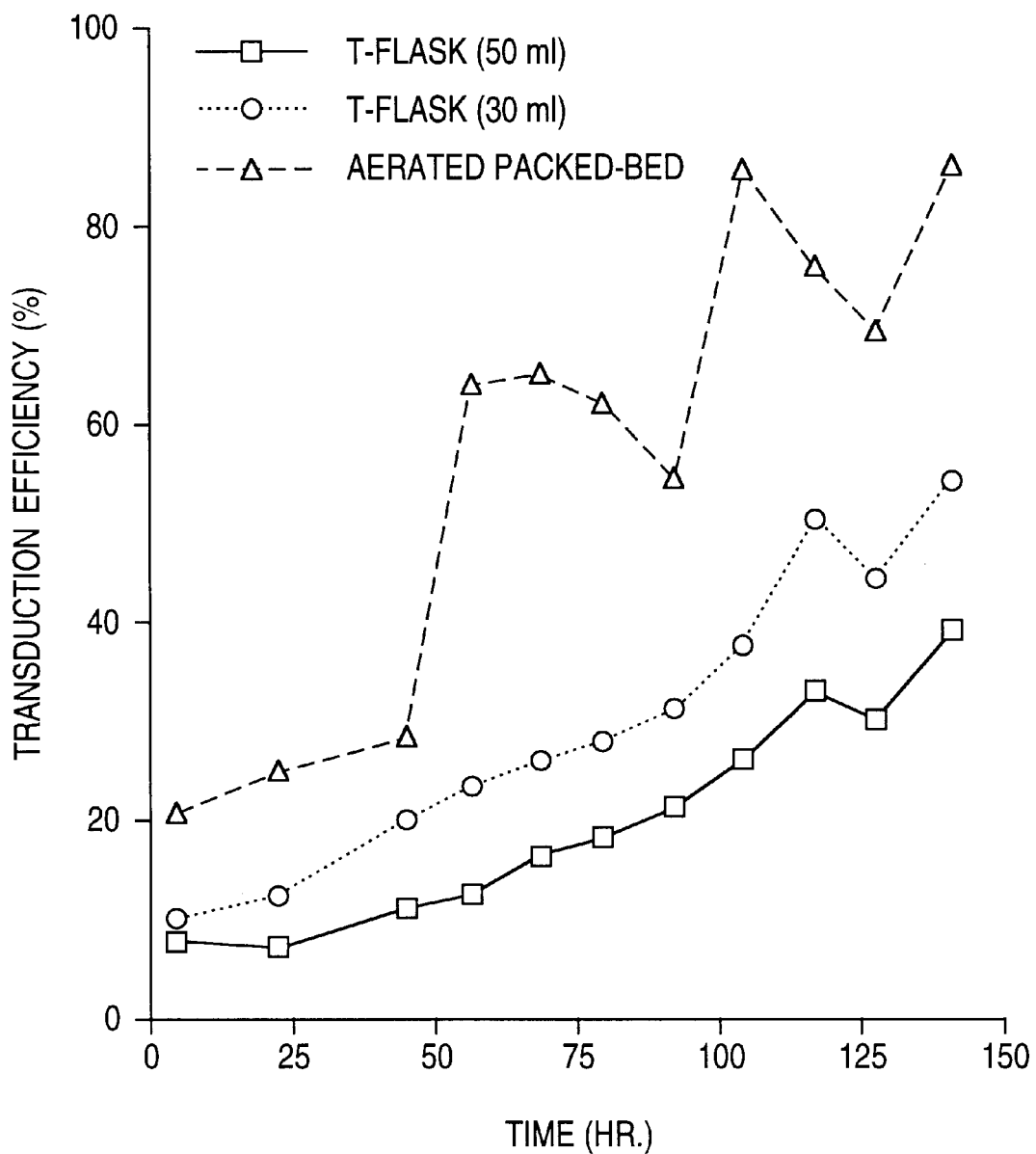
FIG. 15 is the results of the comparison of vector production from ProPak-A-A.855 producer cells in varies T-flasks versus aerated packed-bed bio-reactor, and as measured on 293 cells. Time (h) is in hours. Transduction efficiency is presented as a %.
Figure 16:
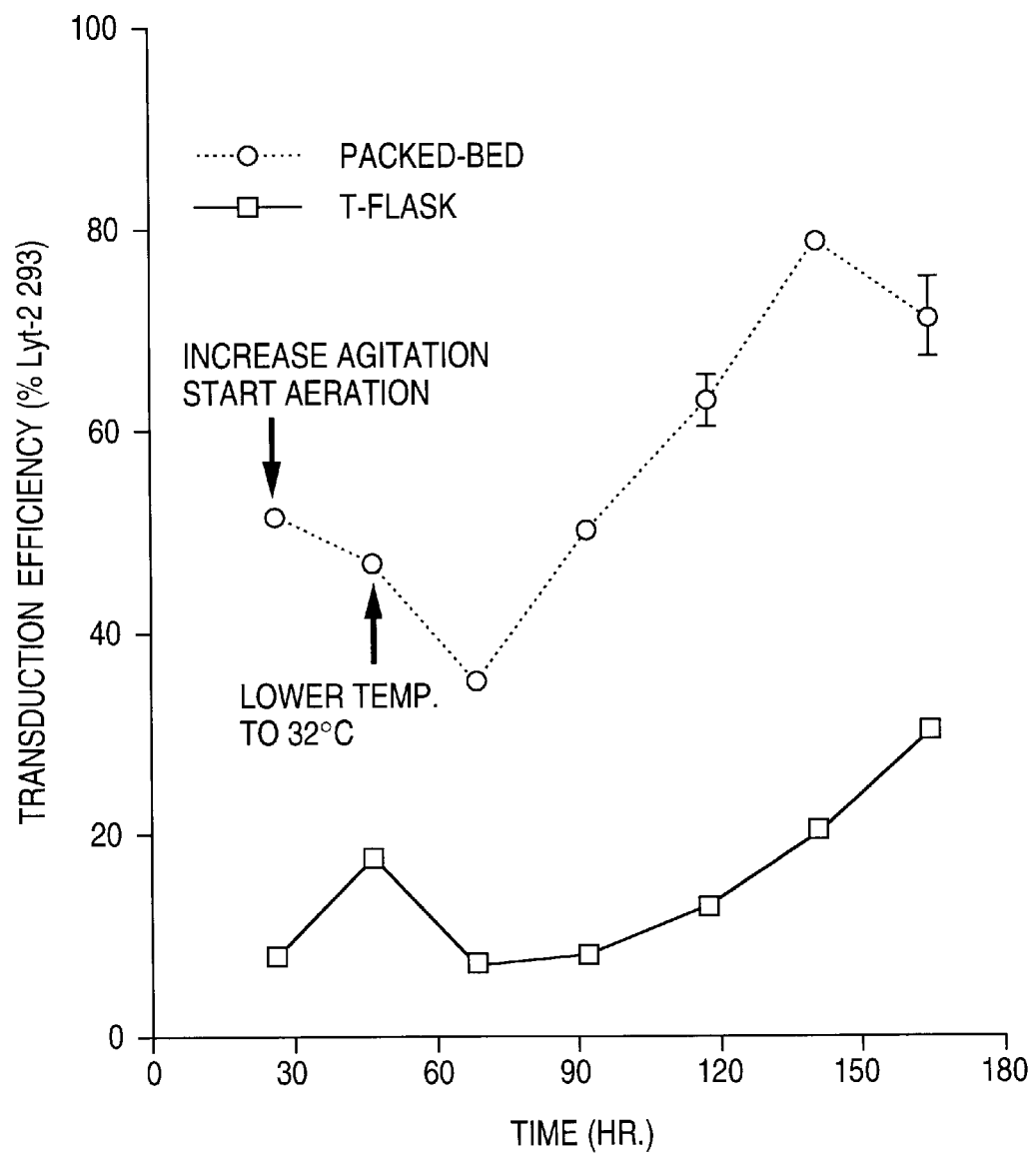
FIG. 16 shows transduction of 293 cells with supernatants harvested at different times post seeding of cells in either a T-flask or the packed-bed bio-reactor.
Figure 17:
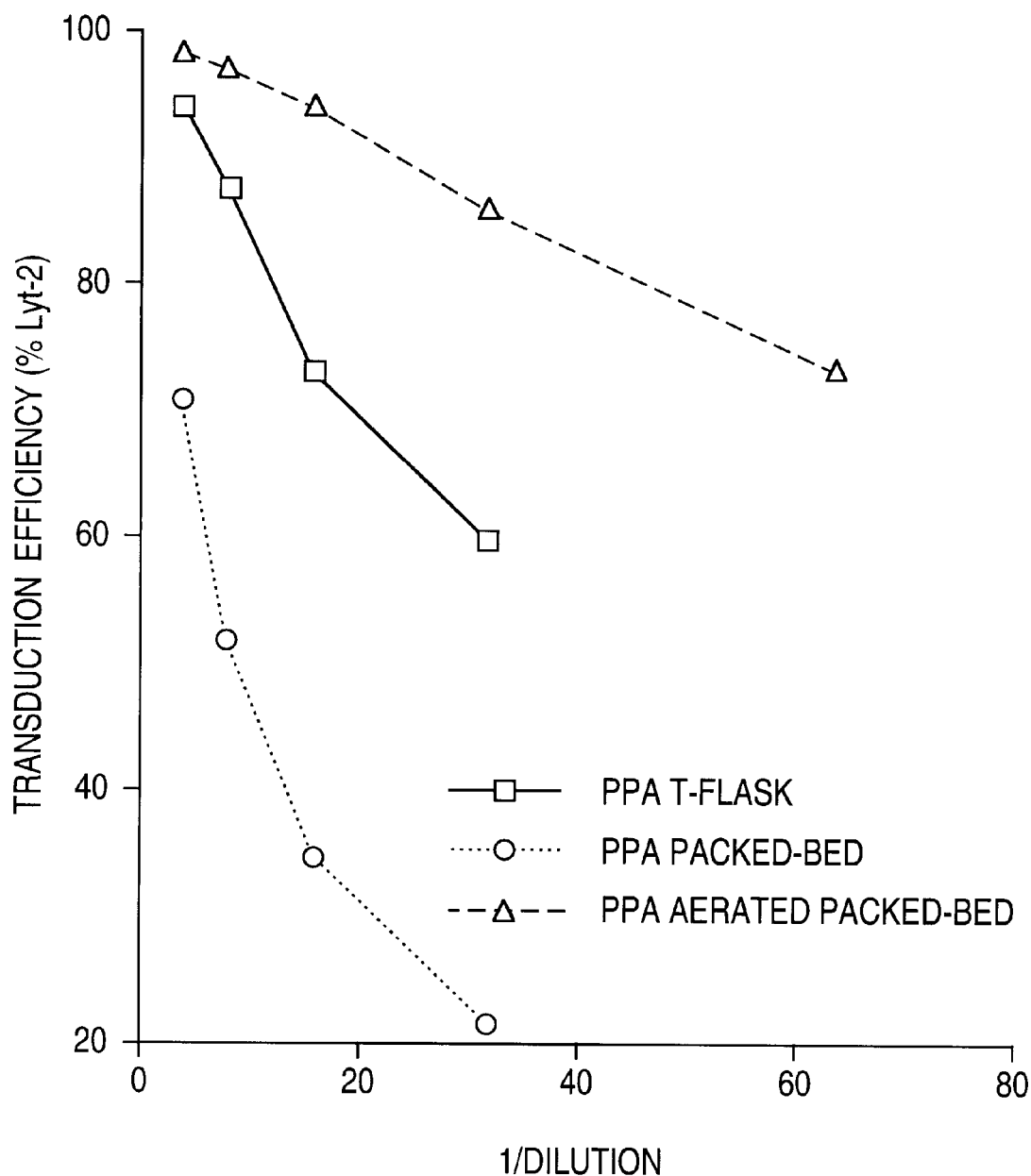
FIG. 17 is a comparison of transduction efficiency achieved with supernatants harvested from ProPak-A-LMiLy cells cultured as shown.

FIG. 15 shows the comparison of virus production from ProPak-A cells culture in T-flasks and in the packed-bed bioreactor with aeration as assayed on 293 cells. The supernatant produced using the packed bed bio-reactore is considerably better than that produced in T-flasks. FIG. 16 shows that ProPak-X cells also produce higher transduction efficiency supernatant when cultured in the packed-bed bioreactoras compared to T-flasks. Dilution of vector supernatant produced by ProPak-A under different culture conditions is shown in FIG. 17. Again, the aerated packed-bed bioreactorproduces higher quality vector supernatants as determined by transduction efficiency.

EXAMPLE 5

Primary Cell Transductions Cell selection and analysis

Apheresed samples were obtained with informed consent from multiple myeloma or breast cancer patients. Stem cells were mobilized into the peripheral blood by treatment with cyclophosphamide (Cytoxan) and GM-CSF (multiple myeloma), G-CSF above (breast cancer), or Cytoxan+VP-16+CDDP+G-CSF (breast cancer). Apheresis for total white cells was started when the peripheral blood white cell count was greater than 500 cells/ml and the platelet count was greater than 50,000 cells/ml. Patients were apheresed daily until 6×10$^8$ mononuclear cells (MNC) were collected.

The cells were washed twice in PBS (partially depleting platelets), and CD34+ cells were positively selected using a Baxter Isolex cell selector. The recovered cells averaged 85% pure as determined by FACS analysis.

Transduction $0.5 \times 10^6$ viable CD34+ cells were suspended in 0.5 ml of freshly thawed retroviral supernatant and diluted 1:2 in Whitlock/Witte media (50% IMDM, 50% RPMI 1640, 10% FCS, $4 \times 10^{-5}$M 2-mercaptoethanol, 10 mM HEPES, 100µ/ml penicillin, 100 mg/ml streptomycin, and 4 mM glutamine) containing cytokines at the following final concentrations: c-kit ligand (Amgen) 100 ng/ml; IL-3 (Sandoz) 20 ng/ml; IL-6 (Sandoz) 20 ng/ml. Protamine sulfate was added at a final concentration of 4 µg/ml or polybrene was added at a final concentration of 8 µg/ml. The cells and virus were centrifuged at 2800xg, 33° C. to 35° C., for three hours. The cells were resuspended in media with cytokines and cultured for three days. After three days, cells were harvested and approximately $4 \times 10^5$ cells used to determine bulk transduction frequency, and plated in methylcellulose to determine progenitor cell transduction frequency (see below).

Figure 18A:
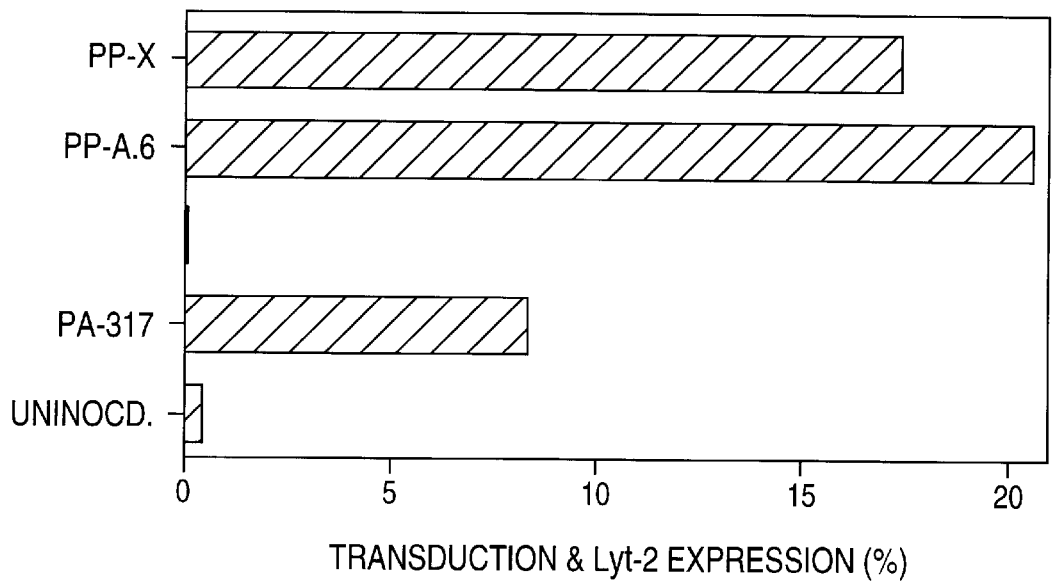
FIGS. 18A and 18B shows transduction of bone marrow (CD34+) with LMiLy packed-bed supernatants.
Figure 18B:
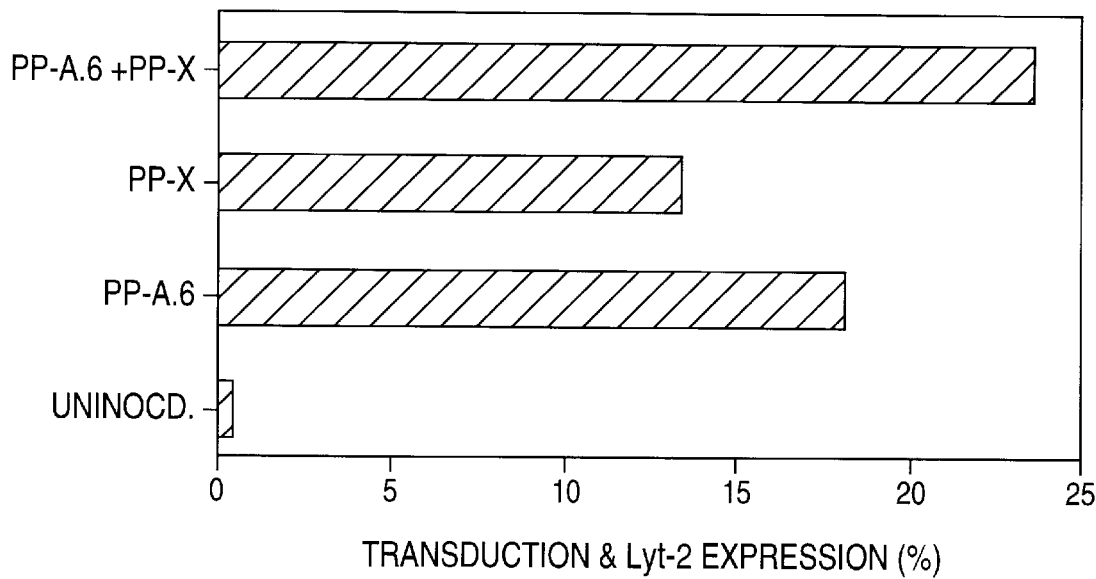

For the LLySN vector, which contains the murine Lyt-2 marker gene, bulk transduction efficiency was determined by staining with APC or PE conjugated anti-Lyt-2 (Pharmingen) and sulfurhodamine conjugated anti-CD34. The results are shown in FIGS. 18A and 18B. Vector supernatant from both ProPak-A and ProPak-X transduced primary human cells with greater efficiency than that from PA317 cells. The combination of amphotropic and xenotropic vector can be useful to deliver two vectors to the same cell since they do not compete for the same receptor.

Methylcellulose assay 2.5 to $10 \times 10^3$ cells from each transduction were added to 4 ml of methylcellulose (Stem Cell Technologies) plus 1 ml IMDM containing the following cytokines (final concentration): c-kit ligand 100 ng/ml; GM-CSF (Amgen) 10 ng/ml; IL-3 10 ng/ml; IL-6 10 ng/ml; rhEPO (Amgen) 2 units/ml. 1.0 ml of the cell/cytokine methylcellulose mixture was plated onto five 35 mm plates using a 5 ml syringe and 16 gauge needle, and the plates were placed in a 37° C. incubator for 2 weeks.

After 14 days, single methylcellulose colonies were picked and analyzed for the presence of neo or RevM10 by PCR.

Analysis

Individual colonies are picked by aspiration in 5 µl and suspended in 500 µl PBS. The cells are pelleted and resuspended in 50 µl buffer A (100 mM KCl, 10 mM Tris pH 8.2, 2.5 mM $MgCl_2$). 50 µl Lysis Buffer (10 mM Tris pH 8.3, 2.5 mM $MgCl_2$, 1% Tween 20, 1% NP40, 100 µl/ml proteinase K) is added, and the mixture allowed to incubate overnight at 37° C. or for 2 h at 56° C. The proteinase K is inactivated by heating at 94° C. for 10 min, and 10 µl of the lysate is used for the PCR reaction.

The PCR reaction amplified a 100 bp fragment of the β-globin gene and either a 240 bp fragment of the neo gene or a 180 bp fragment of RevM10, depending on the vector used. The primers used were as follows.

Rev: 5'TCgATTAgTgAACggATCCTT 3' (SEQ. ID NO. 5)

5'CTCCtgACTCCAATATTgCAg 3' (SEQ. ID NO. 6)

Neo: 5'TCgACgTTgTCACTgAAgCg 3' (SEQ. ID NO. 7)

5'gCTCTTCgTCCAgATCATCC 3' (SEQ. ID NO. 8)

Beta-globin: 5'ACACAACTgTgTTCACTAgC 3' (SEQ. ID NO. 9)

5'CAACTTCATCCACgTTCACC 3' (SEQ. ID NO. 10)

The reactions were performed in a 40 µl final volume in a Perkin Elmer thermal cycler 9600 as follows: 5 min denaturation at 94° C.; 40 cycles of 30 sec at 94° C., 30 sec at 62° C., 1 min at 72° C.; and 10 min at 72° C. PCR products are visualized by ethidium bromide agarose gel electrophoresis (Sambrook et al. (1989) supra) and the PCR products confirmed by Southern blot hybridization. A sample is considered positive if the Rev or neo band is equal or stronger in intensity than the β-globin band. Results are summarized in FIG. 14. Results shown in FIG. 16 show that both the xenotropic ProPak-X and the amphotropic ProPak-A are able to produce retroviral vector preparations which transduce human hematopoietic stem/progenitor cells with higher efficiency than that produced from standard PA317 cells.

As is apparent to those of skill in the art, various modifications and alterations to the above can be made without departing from the spirit and scope of the invention disclosed herein. Accordingly, the invention is limited only by the following claims.

What is claimed is:

1. A method for obtaining a recombinant retroviral packaging cell capable of producing retroviral vectors comprising:
   a. selecting a retrovirus;
   b. obtaining a eukaryotic cell free of endogenous retroviral nucleic acid of the same type as the retrovirus of step (a);
   c. preparing a minimal gag-pol open reading frame (ORF) insert from the retrovirus wherein the ORF contains no flanking sequences of the gag-pol gene;
   d. inserting the minimal gag-pol ORF prepared from step (c) into an appropriate expression plasmid, wherein the gag-pol ORF is operatively linked to a heterologous promoter having no overlap with the retroviral vector;
   e. preparing a minimal env open reading frame (ORF) insert from the retrovirus wherein the ORF contains no flanking sequences of the env gene;
   f. inserting the minimal env ORF prepared from step (e) into an appropriate expression plasmid, wherein the env ORF is operatively linked to a heterologous promoter having no overlap with the retroviral vector;
   g. inserting the expression plasmids of steps (d) and (f) into the cell of step (b);
   h. propagating the cell obtained from step (g) under conditions favorable for expression of the minimal retroviral gag-pol and env ORF; and
   i. screening a cell for retroviral Gag, Pol and Env production by the cell of step (h); thereby obtaining the retroviral packaging cell capable of packaging recombinant retroviral vector sequences to produce recombinant, transducing retrovirus.

2. The method of claim 1, wherein the retrovirus is a Moloney murine leukemia virus.

3. The method of claim 1, wherein the cell is a non-murine cell.

4. The method of claim 3, wherein the non-murine cell is a primate cell.

5. The method of claim 4, wherein the primate cell is a human cell.

6. The method of claim 3, wherein the non-murine cell is selected from the group consisting of Vero, HT-1080, D17 MRC-5, FS-4, TEG71, human embryonic kidney (293), and HeLa.

7. The method of claim 6, wherein the human embryonic kidney cells are 293 cells (ATCC CRL 1573).

8. The method of claim 1, wherein the gag-pol ORF is a moloney murine leukemia virus gag-pol gene.

9. The method of claim 8, wherein the gag-pol gene is expressed from the CMV-IE promoter or the RSV-LTR promoter.

10. The method of claim 1, wherein the env ORF is a moloney murine leukemia virus env gene.

11. The method of claim 1, wherein the plasmid of steps (d) or (f) comprises a selectable or detectable marker gene.

12. The method of claim 1, wherein the gag-pol ORF and the env ORF expression plasmids of step (g) are amplified in bacterial host cells prior to inserting into the eukaryotic cell of step (b), wherein the bacterial host cells are propagated at a temperature range from about 28° C. to about 32° C.

13. The method of claim 12, wherein the bacterial host cells are propagated at about 30° C.

14. The method of claim 1, wherein in step (i), Gag, Pol and Env production is screened by a sandwich ELISA assay.

15. The method of claim 14, wherein
   Env is detected using a primary antibody from hybridoma 83A25 followed by antiserum 79S-834, enzyme-conjugated antispecies antibody and enzyme substrate; and
   Gag is detected separately using a primary antibody from hybridoma R187 followed by antiserum 77S-227, enzyme-conjugated antispecies antibody and enzyme substrate.

16. The recombinant retroviral packaging cell obtained by the method of claim 1.

17. The recombinant retroviral packaging cell of claim 16, wherein the cell produces an amphotropic env.

18. The recombinant retroviral retroviral packaging cell of claim 16, wherein the cell produces a xenotropic env.

19. A retroviral packaging cell line designated ProPak-A.6 having ATCC Accession No. CRL 12006.

20. A method of producing a retroviral producer cell which comprises transducing the cells of claim 16 with a retroviral-based vector and subsequently propagating the cells under conditions favorable for the production and secretion of retroviral vector supernatant.

21. The method of claim 20, further comprising screening the producer cell for the ability to produce a vector supernatant having high transduction efficiency, comprising measuring the ability of the vector supernatant to transduce a target cell population with a transduction efficiency greater than that achieved with a vector supernatant produced from murine PA317-based cells.

22. The method of claim 21, wherein the target cell population is human 293 cells.

23. The retroviral producer cell produced by the method of claim 20.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (xi) SEQUENCE DESCRIPTION: SEQ ID NO:1:

AAAAAAAAGC GGCCGCGCCG CCACCATGGG CCAGACTGTT ACCAC      45

(2) INFORMATION FOR SEQ ID NO:2:

```
        (i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:2:

AAAAAAAAGC GGCCGCTCAT TAGGGGGCCT CGCGGG                              36

(2) INFORMATION FOR SEQ ID NO:3:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:3:

TAATCTACGC GGCCGCCACC ATGGCGCGTT CAACGCTC                            38

(2) INFORMATION FOR SEQ ID NO:4:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:4:

AATGTGATGC GGCCGCTCAT GGCTCGTACT CTATGG                              36

(2) INFORMATION FOR SEQ ID NO:5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:5:

TCGATTAGTG AACGGATCCT T                                              21

(2) INFORMATION FOR SEQ ID NO:6:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:6:

CTCCTGACTC CAATATTGCA G                                              21

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:7:

TCGACGTTGT CACTGAAGCG                                                20

(2) INFORMATION FOR SEQ ID NO:8:

(i) SEQUENCE CHARACTERISTICS:
            (A) LENGTH: 20 base pairs
```

```
        (B) TYPE: nucleic acid
        (C) STRANDEDNESS: single
        (D) TOPOLOGY: linear (xi) SEQUENCE DESCRIPTION: SEQ ID NO:8:

GCTCTTCGTC CAGATCATCC                                                         20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

ACACAACTGT GTTCACTAGC                                                         20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

CAACTTCATC CACGTTCACC                                                         20
```